United States Patent [19]

Negele et al.

[11] Patent Number: 4,990,633

[45] Date of Patent: Feb. 5, 1991

[54] FLUORINATED BISARYLOXY-SUBSTITUTED ALKENES, PROCESS FOR THEIR PREPARATION AND THEIR USE

[75] Inventors: Michael Negele, Cologne; Dietmar Beilefeldt, Ratingen; Thomas Himmler, Cologne; Albrecht Marhold, Leverkusen, all of Fed. Rep. of Germany

[73] Assignee: Bayer Aktiengesellschaft, Leverkusen, Fed. Rep. of Germany

[21] Appl. No.: 347,595

[22] Filed: May 4, 1989

[30] Foreign Application Priority Data

May 25, 1988 [DE] Fed. Rep. of Germany ....... 3817626

[51] Int. Cl.[5] .................. C07C 43/205; C07D 303/04; C07D 303/34; C07D 303/36

[52] U.S. Cl. .................................... 549/551; 549/554; 549/559; 549/560; 556/413; 556/414; 556/428; 556/437; 556/438; 556/449; 556/487; 560/15; 560/16; 560/19; 560/60; 560/76; 560/81; 560/83; 560/87; 560/88; 560/116; 560/117; 560/121; 560/125; 560/126; 560/128; 562/426; 562/433; 562/465; 562/470; 564/336; 564/366; 564/372; 564/461; 564/462; 564/500; 564/509; 564/510; 564/511; 564/512; 564/442; 564/443; 564/457; 568/644; 568/645; 558/302

[58] Field of Search ................ 568/645, 644; 549/551, 549/554, 559, 560; 556/413, 414, 437, 438, 428, 449, 487; 564/336, 366, 372, 462, 461, 509, 510, 511, 512, 457, 442, 443; 560/15, 16, 19, 330, 60, 81, 76, 83, 87, 88, 116, 117, 121, 125, 126, 128; 562/426, 433, 465, 470; 558/302

[56] References Cited

FOREIGN PATENT DOCUMENTS 0333158 4/1968 U.S.S.R. .

OTHER PUBLICATIONS

Card et al., "Reactions of Perfluorocycloalkenones with Nucleophiles", CA 93:204115w (1980).

The Journal of Organic Chemistry, vol. 45, No. 22, Oct. 24, 1980, pp. 4429–4432.

Chemical Abstracts, vol. 62, Feb. 1965, pp. 2715–2716, 2716f–g.

*Primary Examiner*—Glennon H. Hollrah
*Assistant Examiner*—Amelia A. Owens
*Attorney, Agent, or Firm*—Sprung Horn Kramer & Woods

[57] ABSTRACT

New fluorinated bisaryloxy-substituted alkenes are prepared by reaction of substituted phenols with perhaloalkenes and can be used as electrical insulating agents.

6 Claims, No Drawings

FLUORINATED BISARYLOXY-SUBSTITUTED ALKENES, PROCESS FOR THEIR PREPARATION AND THEIR USE

The present invention relates to new fluorinated bisaryloxy-substituted alkenes, a process for their preparation by reaction of specifically substituted phenols with specific perhaloalkenes in basic medium and in the presence of solvents and, if appropriate, subsequent derivatization or rederivatization, and the use of fluorinated bisaryloxy-substituted alkenes as electrical insulating agents.

The substitution of both vinylic halogen atoms in dihaloperfluoroalkenes by phenols or by phenoxides is as yet illustrated by a single example: under specific conditions (−40° C., mmol scale, complicated distillation) 1,2-bisphenoxy-3,3,4,4,5,5-hexafluorocyclopent-1-ene could be prepared in 76% yield from sodium phenoxide and octafluorocyclopentene in ethylene glycol dimethyl ether (see J.O.C. 45, 4429 (1980). Based on the other existing literature (for example Fluorine in Organic Chemistry, Wiley, 1973), it could not be concluded that this reaction could underlie a generally applicable synthesis principle. Thus, only monoaryloxy-perfluorocyclobutenes were obtained by reaction of phenol or 2-naphthol with hexafluorocyclobutene in ether using equimolar amounts of triethylamine (see J.A.C.S. 72, 4480 (1950).

In the reaction of phenol with 1,2-dichloro-3,3,4,4,5,5-hexafluorocyclopent-1-ene in dimethylformamide in the presence of equimolar amounts of potassium hydroxide, 58.8% of monosubstitution products, 3.4% of geminal disubstitution products and 45.8% of trisubstitution products were detected in the reaction product (see Can. J. Chem. 53, 2302 (1975)). None of the geminal disubstitution products mentioned there correspond to those of the present invention. From the same reference, it follows that with the use of p-nitrothiophenol instead of phenol the corresponding disubstitution product (a bisarylthio-substituted alkene) is obtained in good yields.

The reaction of o-aminophenol with octafluorocyclopentene in acetonitrile in the presence of potassium carbonate leads to 2-heptafluorocyclopentyl-1-oxyaniline, a monoaryloxy-substituted alkene. On analogous reaction with o-aminothiophenol instead of o-aminophenol a bisarylthiosubstituted cyclopentene is obtained as intermediate (J. C. S. Perkin Trans. I 763 1987).

It thus follows from the prior art that only fluorinated bisarylthio-substituted alkenes are easily accessible and fluorinated bisaryloxy-substituted alkenes of other types than those according to the invention are for the most part only accessible in traces in addition to large amounts of mono- and tri-substituted products. It could not therefore be expected that the fluorinated bisaryloxysubstituted alkenes according to the invention are existent and easily accessible.

Now fluorinated bisaryloxy-substituted alkenes have been found of the formula (I)

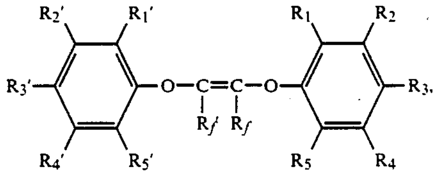

(I)

in which $R_f$ and $R_f'$ independently of one another represent a to $C_6$-perfluoroalkyl radical or $R_f$ and $R_f'$ together represent a $C_2$- to $C_4$perfluoroalkylene radical and $R_1$ to $R_5$ and $R_1'$ to $R_5'$ independently of one another represent hydrogen, $C_1$- to $C_{12}$-alkyl, $C_2$- to $C_6$-alkenyl and/or $C_2$- to $C_6$alkinyl, which are optionally substituted with OCN—, $R_6O$-, $H_2N$—, $R_6SO_3^-$and/or $R_6OOC$— groups (with $R_6$=hydrogen or optionally substituted $C_1$- to $C_6$-alkyl or optionally substituted $C_5$- to $C_7$-cycloalkyl and where alkinyl groups may also contain silyl substituents, $C_1$- to $C_4$haloalkyl, $C_1$- to $C_4$-epoxyalkyl, $C_1$- to $C_4$-hydroxyalkyl, optionally substituted phenyl, —$OR_7$ (with $R_7$=hydrogen, $C_1$- to $C_6$-alkyl, $C_1$- to $C_4$-hydroxyalkyl, $C_1$- to $C_4$-epoxyalkyl, '—(—$CH_2$)$_m$[—O—(—$CH_2$)$_m$—]—$_n$OH with m=1 to 4 and n=1 to 8, optionally substituted phenyl or optionally substituted benzyl), halogen, $NO_2$, $NH_2$, NCO, CN, $SO_3X$ (with X=hydrogen, sodium or potassium), S—$C_1$to $C_6$-alkyl, $SO_2$halogen, optionally substituted $C_5$- to $C_7$-cycloalkyl, carbonyl$R_8$ (with $R_8$=hydrogen, optionally substituted $C_1$- to $C_6$-alkyl, optionally substituted $C_5$- to $_7$-cycloalkyl, halogen, optionally substituted $C_1$- to $C_6$-alkoxy, optionally substituted $C_5$ to $C_7$-cycloalkoxy or OY with Y=hydrogen, sodium or potassium) or $$\overset{|}{(R_9CO)N(R_{10})}$$

(with $R_9$=$C_1$- to $C_6$-alkyl, $C_1$- to $C_4$haloalkyl, optionally substituted phenyl or hydrogen and with $R_{10}$=hydrogen or $C_1$- to $C_4$-alkyl), where the compound is excluded in which $R_1$ to $R_5$ and $R_1'$ to $R_5'$ represent hydrogen and $R_f$ and $R_f'$ together represent —(—$CF_2$—)—$_3$.

If $R_f$ and $R_f'$ together represent a perfluoroalkylene radical, $R_f$, $R_f'$ and the two C atoms in between form a 4- to 6-membered perfluorocycloalkyl group.

$C_2$- to $C_6$-alkenyl and -alkinyl radicals may contain one or more multiple bonds which may be arranged in an internal position or a terminal position. Preferably, only one multiple bond is contained which is preferably arranged in a terminal position.

$C_1$- to $C_4$-haloalkyl radicals may be radicals having one or more identical or different halogen atoms. Possible halogen atoms are fluorine, chlorine, bromine and/or iodine, fluorine, chlorine and/or bromine being preferred, in particular fluorine and/or chlorine. The halogen atom or atoms may be arranged in an internal position or a terminal position.

$C_1$- to $C_4$-epoxy and $C_1$- to $C_4$-hydroxyalkyl radicals (as $R_1$ to $R_5$, $R_1'$ to $R_5'$ and/or as $R_6$) preferably contain only one epoxy or one hydroxyl group. This is preferably in a terminal position arrangement.

Inasmuch as phenyl radicals (as $R_1$ to $R_5$, $R_1'$ to $E_5'$ and/ or as $R_6$) may be substituted, possible substituents are, for example, $NO_2$, $NH_2$, NCO, COOH, CHO, OH, $SO_3H$, F, Cl and/or Br.

Inasmuch as benzyl radicals may be substituted, possible substituents are the same as in substituted phenyl radicals.

Halogen radicals may be fluorine, chlorine, bromine or iodine atoms. Fluorine, chlorine and bromine atoms are preferred, in particular fluorine and chlorine atoms.

$SO_2$-halogen radicals may contain, for example, fluorine, chlorine or bromine as halogen. Fluorine and chlorine are preferred.

Inasmuch as $C_5$- to $C_7$-cycloalkyl radicals may be substituted, possible substituents are, for example, $C_1$- to $C_6$-alkyl, $C_2$- to $C_6$-alkenyl, $C_1$- to $C_4$-haloalkyl, optionally substituted phenyl, halogen, $NH_2$, COOH or OH.

The radicals $R_1$ to $R_5$ may be identical or completely or partly different from one another. Independently of the meaning of $R_1$ to $R_5$, the radicals $R_1'$ to $R_5'$ may also be identical or completely or partly different from one another.

Fundamentally, $R_f$ and $R_f'$ are preferably identical and represent $CF_3$ (where the two $CF_3$ groups may be present in the cis- or trans-configuration with reference to the central C=C double bond in formula (I) or $R_f$ and $R_f'$ together from a $-CF_2-CF_2'$ or a $-CF_2-CF_2-CF_2-$ group.

Fundamentally, in each case $R_1$ and $R_1'$ and independently thereof in each case $R_5$ and $R_5'$ are preferably identical and represent hydrogen, $C_1$- to $C_4$-alkyl, $C_1$- to $C_4$-haloalkyl, $NO_2$, NCO, fluorine or chlorine. $R_1$, $R_1'$, $R_5$ and $R_5'$ are particularly preferably identical and represent hydrogen or chlorine, in particular hydrogen, or $R_1$ and $R_1'$ represent hydrogen and $R_5$ and $R_5'$ represent $CF_3$.

Fundamentally, in each case $R_2$ and $R_2'$ and independently thereof in each case $R_4$ and $R_4'$ are preferably identical and represent hydrogen, $C_1$- to $C_4$-alkyl, COOH, fluorine, chlorine or $C_1$- to $C_4$-haloalkyl. $R_2$, $R_2'$, $R_4$ and $R_4'$ are particularly preferably identical and represent hydrogen, chlorine or $CF_3$ or $R_2$ and $R_2'$ represent hydrogen and $R_4$ and $R_4'$ represent $CH_3$.

Fundamentally, $R_3$ and $R_3'$ independently of one another preferably represent hydrogen, $C_1$- to $C_{12}$-alkyl, $C_2$to $C_6$-alkenyl and/or $C_2$- to $C_6$-alkinyl, which are optionally substituted by OCN—, $R_6O$—, $H_2N$—, $R_6SO_3$— and/ or $R_6OOC$— groups (with $R_6$=hydrogen or optionally substituted $C_1$- to $C_6$-alkyl or optionally substituted $C_5$- to $C_7$-cycloalkyl) and where alkinyl groups may also contain silyl substituents, in particular trimethylsilyl substituents, $C_1$- to $C_4$-haloalkyl, $C_1$- to $C_4$-epoxyalkyl, $C_1$to $C_4$-hydroxyalkyl, optionally substituted phenyl, $-OR_7$ (with $R_7$=hydrogen, $C_1$- to $C_6$-alkyl, $C_1$- to $C_4$-hydroxyalkyl, $C_1$- to $C_4$-epoxyalkyl, $-(-CH_2)_m-[-O-(CH_2)_m-]-_nOH$ with m=1 to 4 and n=1 to 8, optionally substituted phenyl or optionally substituted benzyl), halogen, $NO_2$, $NH_2$, NCO, CN, $SO_3X$ (with X=hydrogen, sodium or potassium), S-$C_1$- to $C_6$-alkyl, $SO_2$-halogen, optionally substituted $C_5$- to $C_7$-cycloalkyl, carbonyl-$R_8$ (with $R_8$=hydrogen, optionally substituted $C_1$- to $C_6$-alkyl, optionally substituted $C_5$- to $C_7$-cycloalkyl, halogen, optionally substituted $C_1$- to $C_6$-alkoxy, optionally substituted $C_5$- to $C_7$-cycloalkoxy or OY with Y=hydrogen, sodium or potassium) or $$\overset{|}{(R_9CO)N(R_{10})}$$

(with $R_9$=$C_1$- to $C_6$-alkyl, $C_1$- to $C_4$-haloalkyl, optionally substituted phenyl or hydrogen and with $R_{10}$=hydrogen or $C_1$- to $C_4$-alkyl).

Fundamentally, $R_3$ and $R_3'$ are particularly preferably identical and represent hydrogen, $C_1$- to $C_{12}$-alkyl, ethenyl, ethinyl, $CF_3$, $C_2$- to $C_3$-epoxyalkyl, $C_1$- to $C_3$-hydroxyalkyl, OH, O-$C_1$- to $C_3$-alkyl, O-benzyl, fluorine, chlorine, bromine, $NO_2$, $NH_2$, NCO, S-$C_1$- to $C_3$-alkyl, COOH, CHO, CO-$C_1$- to $C_3$-alkyl, COCL or CO-O-$C_1$- to $C_3$alkyl.

Specifically preferred individual compounds of the formula (I) are summarized in Table 1.

TABLE 1

| $R_f$ $R_f'$ | Other substituents (unspecified = H) |
|---|---|
| $-(CF_2)_2-$ | $R_3 = R_3' = -NO_2$ |
| $-(CF_2)_2-$ | $R_3 = R_3' = -NH_2$ |
| $-(CF_2)_2-$ | $R_3 = R_3' = -NCO$ |
| $-(CF_2)_2-$ | $R_3 = R_3' = -CN$ |
| $-(CF_2)_2-$ | $R_3 = R_3' = -COOH$ |
| $-(CF_2)_2-$ | $R_3 = R_3' = -CO-OCH_3$ |
| $-(CF_2)_2-$ | $R_3 = R_3' = -CO-O$-(L)-Menthyl |
| $-(CF_2)_2-$ | $R_3 = R_3' = -OH$ |
| $-(CF_2)_2-$ | $R_3 = R_3' = -CHO$ |
| $-(CF_2)_2-$ | $R_3 = R_3' = -OCH_2-$ 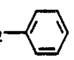 |
| $-(CF_2)_2-$ | $R_3 = R_3' = -NH-COCH_3$ |
| $-(CF_2)_2-$ | $R_3 = R_3' = -Cl$ |
| $-(CF_2)_2-$ | $R_3 = R_3' = -Br$ |
| $-(CF_2)_2-$ | $R_1 = R_1' = -CF_3$; $R_3 = R_3' = -NO_2$ |
| $-(CF_2)_2-$ | $R_1 = R_1' = -CF_3$; $R_3 = R_3' = -NH_2$ |
| $-(CF_2)_2-$ | $R_1 = R_1' = -CF_3$; $R_3 = R_3' = -NCO$ |
| $-(CF_2)_3-$ | $R_3 = R_3' = -CH_3$ |
| $-(CF_2)_3-$ | $R_3 = R_3' = -NO_2$ |
| $-(CF_2)_3-$ | $R_3 = R_3' = -C_9H_{19}$ |
| $-(CF_2)_3-$ | $R_2 = R_2' = R_3 = R_3' = -CH_3$ |
| $-(CF_2)_3-$ | $R_3 = R_3' = -NH_2$ |
| $-(CF_2)_3-$ | $R_3 = R_3' = -OCH_3$ |
| $-(CF_2)_3-$ | $R_3 = R_3' = -NCO$ |
| $-(CF_2)_3-$ | $R_3 = R_3' = -OCH_2-$ 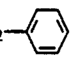 |
| $-(CF_2)_3-$ | $R_1 = R_1' = R_3 = R_3' = Cl$; $R_2 = R_2' = NO_2$ |
| $-(CF_2)_3-$ | $R_3 = R_3' = -CO-OCH_3$ |
| $-(CF_2)_3-$ | $R_3 = R_3' = -COOH$ |
| $-(CF_2)_3-$ | $R_3 = R_3' = -COCl$ |
| $-(CF_2)_3-$ | $R_3 = R_3' = -OH$ |
| $-(CF_2)_3-$ | $R_3 = R_3' = -Cl$ |
| $-(CF_2)_3-$ | $R_3 = R_3' = -CHO$ |
| $-(CF_2)_3-$ | $R_3 = R_3' = -Br$ |
| $-(CF_2)_3-$ | $R_3 = R_3' = -CH_2OH$ |
| $-(CF_2)_3-$ | $R_3 = R_3' = -F$ |
| $-(CF_2)_3-$ | $R_1 = R_1' = -CF_3$; $R_3 = R_3' = -NO_2$ |
| $-(CF_2)_3-$ | $R_2 = R_2' = R_3 = R_3' = -COOH$ |
| $-(CF_2)_3-$ | $R_3 = R_3' = -COONa$ |
| $-(CF_2)_3-$ | $R_3 = R_3' = -SCH_3$ |
| $-(CF_2)_3-$ | $R_2 = R_2' = R_4 = R_4' = -CF_3$ |
| $-(CF_2)_3-$ | $R_3 = CH_3$; $R_3' = -NO_2$ |
| $-(CF_2)_3-$ | $R_1$ bis $R_5 = R_1'$ bis $R_5' = -Cl$ |
| $-(CF_2)_3-$ | $R_3 = R_3'$ = Ethinyl |
| $-(CF_2)_3-$ | $R_3 = R_3'$ = Ethenyl |
| $-(CF_2)_3-$ | $R_3 = R_3' =$ 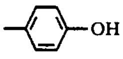 —OH |
| $-(CF_2)_3-$ | $R_3 = R_3'$ = Ethylenoxy |
| $-(CF_2)_3-$ | $R_2 = R_2' = R_3 = R_3' = -CF_3$ |
| $-(CF_2)_3-$ | $R_1 = R_1' = -CF_3$ |

TABLE 1-continued

| $R_f$ | $R_f'$ | Other substituents (unspecified = H) |
|---|---|---|
| $-(CF_2)_3-$ | | $R_3 = R_3' =$ 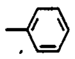 |
| $-(CF_2)_3-$ | | $R_3 = R_3' =$ 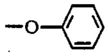 |
| $-(CF_2)_3-$ | | $R_3 = R_3' =$ Methylethenyl |
| $-(CF_2)_3-$ | | $R_3 = R_3' = -CO-CH_2-$ 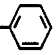 |
| $-(CF_2)_3-$ | | $R_3 = R_3' =$ 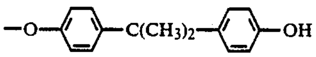 |
| $-(CF_2)_3-$ | | $R_3 = R_3' = -CO-OC_5H_{11}$ |
| $-(CF_2)_3-$ | | $R_3 = R_3' = -NH-COOCH_3$ |
| $-(CF_2)_3-$ | | $R_3 = R_3' = -CO-O$-(L)-Menthyl |
| $-(CF_2)_3-$ | | $R_3 = R_3' = -CN$ |
| $-(CF_2)_3-$ | | $R_3 = R_3' =$ -Propylenoxy |
| $-(CF_2)_3-$ | | $R_3 = R_3' = -OCH_2CH_2OH$ |
| $-(CF_2)_3-$ | | $R_3 = R_3' =$ 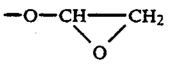 |
| $-(CF_2)_3-$ | | $R_3 = R_3' = -SO_3H$ |
| $-(CF_2)_3-$ | | $R_3 = R_3- = -SO_3Na$ |
| $-(CF_2)_3-$ | | $R_3 = R_3' = -SO_2Cl$ |
| $-(CF_2)_3-$ | | $R_3 = R_3' = -C(CH_3)=CH_2$ |
| $-(CF_2)_3-$ | | $R_3 = R_3' = -CH=CH-CO-OC_2H_5$ |
| $-(CF_2)_3-$ | | $R_3 = R_3' = -CH=CH-CO-NH_2$ |
| $-(CF_2)_3-$ | | $R_3 = R_3' = -CH=CH-CN$ |
| $-(CF_2)_3-$ | | $R_3 = R_3' = -CH=CH-COOH$ |
| $-(CF_2)_3-$ | | $R_3 = R_3' = -C{\equiv}C-C(CH_3)_2OH$ |
| $-(CF_2)_3-$ | | $R_3 = R_3' = -C{\equiv}C-Si-(-CH_3)_3$ |
| $-(CF_2)_3-$ | | $R_3 = R_3' = -C{\equiv}C-$ 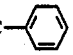 |
| $-(CF_2)_3-$ | | $R_3 = -CH_3; R_3' = -NH_2$ |
| $-(CF_2)_3-$ | | $R_3 = -COOH; R_3' = -NH_2$ |
| $-(CF_2)_3-$ | | $R_3 = -CN; R_3' = -CO-OCH_3$ |
| $-(CF_2)_3-$ | | $R_3 = -CN; R_3' = -CO-O$-(L)-Menthyl |
| $-(CF_2)_3-$ | | $R_3 = -C{\equiv}CH; R_3' = -CO-OCH_3$ |
| $-(CF_2)_3-$ | | $R_3 = -C{\equiv}CH; R_3' = -CO-O$-(L)-Menthyl |
| $-(CF_2)_3-$ | | $R_2 = R_2 = -NH_2; R_3 = R_3' = -OH$ |
| $-(CF_2)_3-$ | | $R_1 = R_1' = R_3 = R_3' = -NO_2$ |
| $-(CF_2)_3-$ | | $R_1 = R_1' = R_3 = R_3' = -NH_2$ |
| $-(CF_2)_3-$ | | $R_1 = R_1' = R_3 = R_3' = -NCO$ |
| $-(CF_2)_3-$ | | $R_1 = R_1' = R_3 = R_3' = R_4 = R_4' = Cl$ |
| $-(CF_2)_3-$ | | $R_1 = R_1' = R_3 = R_3' = Cl$ |
| $-(CF_2)_3-$ | | $R_2 = R_2' = NO_2; R_3 = R_3' = -OCH_3$ |
| $-(CF_2)_3-$ | | $R_1 = R_1' = CF_3; R_3 = R_3' = -NH_2$ |
| $-(CF_2)_3-$ | | $R_1 = R_1' = CF_3; R_3 = R_3' = -NCO$ |
| $-(CF_2)_3-$ | | $R_2 = R_2' = R_3 = R_3' = -COOH$ |
| $-(CF_2)_3-$ | | $R_2 = R_2' = -CO-OCH_3$ |
| $-(CF_2)_3-$ | | $R_2 = R_2' = -COOH$ |
| $-(CF_2)_3-$ | | $R_2 = R_2' = -COCl$ |
| $-(CF_2)_3-$ | | $R_2 = R_2' = -NO_2$ |
| $-(CF_2)_3-$ | | $R_2 = R_2' = -NH_2$ |
| $-(CF_2)_3-$ | | $R_2 = R_2' = -NCO$ |
| $-(CF_2)_3-$ | | $R_3 = R_3' =$ 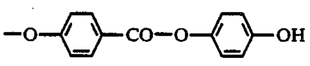 |
| $-(CF_2)_3-$ | | $R_3 = -Br; R_3' = -CN$ |
| $-(CF_2)_3-$ | | $R_3 = -C{\equiv}CH; R_3' = -CN$ |
| $-(CF_2)_3-$ | | $R_3 = -CH = CH-CO-OC_2H_5; R_3' = -CN$ |
| $-(CF_2)_3-$ | | $R_3 = -Br; R_3' = -CO-OCH_3$ |
| $-(CF_2)_3-$ | | $R_3 = -CH=CH-O-OC_2H_5;$ $R_3' = -CO-OCH_3$ |
| $-(CF_2)_3-$ | | $R_3 = CN; R_3' =$ Cyclohexyl |
| $-(CF_2)_4-$ | | $R_3 = R_3' = -NO_2$ |
| $-(CF_2)_4-$ | | $R_3 = R_3' = -NH_2$ |
| $-(CF_2)_4-$ | | $R_3 = R_3' = -NCO$ |

TABLE 1-continued

| $R_f$ | $R_f'$ | Other substituents (unspecified = H) |
|---|---|---|
| $-(CF_2)_4-$ | | $R_3 = R_3' = -CO-OCH_3$ |
| $-(CF_2)_4-$ | | $R_3 = R_3' = -CO-O$-(L)-Menthyl |
| $-(CF_2)_4-$ | | $R_3 = R_3' = -COOH$ |
| $-(CF_2)_4-$ | | $R_3 = R_3' = -CHO$ |
| $-(CF_2)_4-$ | | $R_3 = R_3' = -CN$ |
| $-(CF_2)_4-$ | | $R_3 = R_3' = -NH-COCH_3$ |
| $-(CF_2)_4-$ | | $R_3 = R_3' = -OH$ |
| $CF_3$ | $CF_3$ | $R_3 = R_3' = NO_2$ |
| $CF_3$ | $CF_3$ | $R_3 = R_3' = -NH_2$ |
| $CF_3$ | $CF_3$ | $R_3 = R_3' = -NCO$ |
| $CF_3$ | $CF_3$ | $R_3 = R_3' = -CO-OCH_3$ |
| $CF_3$ | $CF_3$ | $R_3 = R_3' = -COOH$ |
| $CF_3$ | $CF_3$ | $R_3 = R_3' = -OH$ |
| $CF_3$ | $CF_3$ | $R_3 = R_3' = -O-CH_2-$ 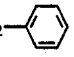 |
| $CF_3$ | $CF_3$ | $R_3 = R_3' = -CN$ |
| $CF_3$ | $CF_3$ | $R_3 = R_3' = -CO-O$-(L)-Menthyl |
| $CF_3$ | $CF_3$ | $R_3 = R_3' = -CHO$ |
| $CF_3$ | $CF_3$ | $R_3 = R_3' = -C{\equiv}CH$ |
| $CF_3$ | $CF_3$ | $R_3 = R_3' = -CH=CH-CO-OC_2H_5$ |
| $CF_3$ | $CF_3$ | $R_2 = R_2' = R_4 = R_4' = CF_3$ |

Compounds of the formula (I) are specifically preferred in which $R_f$ and $R_f'$ in each case represent $CF_3$ or $R_f$ and $R_f'$ together denote a $-CF_2-CF_2-$ or a $-CF_2-CF_2-CF_2$ group, $R_1$, $R_2$, $R_4$, $R_5$, $R_1'$, $R_2'$, $R_4'$ and $R_5'$ represent hydrogen and $R_3$ and $R_3'$ are identical and have a meaning other than hydrogen indicated in claim 3.

The process according to the invention for the preparation of fluorinated bisaryloxy-substituted alkenes of the formula (I) is characterized in that a phenol and/or phenoxide of the formula (II)

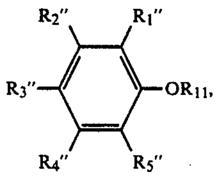

(II)

in which $R_1''$ to $R_5''$ independently of one another represent hydrogen, $C_1$- to $C_{12}$-alkyl, $C_2$- to $C_6$-alkenyl and/or $C_2$- to $C_6$-alkinyl which are optionally substituted by $R_6'O$-, $(R_6')_2N-$, $R_6'SO_3$- and/or $R_6'OOC-$ groups (with $R_6'$=optionally substituted $C_1$- to $C_6$-alkyl or optionally substituted $C_5$- to $C_7$-cycloalkyl) and where alkinyl groups may also contain silyl substituents, $C_1$- to $C_4$-haloalkyl, optionally substituted phenyl, $OR_7'$ (with $R_7'=C_1$- to $C_6$-alkyl, optionally substituted phenyl or optionally substituted benzyl), halogen, $NO_2$, $NH_2$ with non-acidic H atoms, CN, $SO_3X'$ (with X'=sodium or potassium) S-$C_1$to $C_6$-alkyl, optionally substituted $C_5$- to $C_7$-cycloalkyl, carbonyl-$R_8'$ (with $R_8'$=optionally substituted $C_1$to $C_6$-alkyl, $C_1$- to $C_6$-alkoxy, $C_5$- to $C_7$-cycloalkyl or $C_5$-to $C_7$-cycloalkoxy or OY' with Y'=sodium or potassium) or

|
$(R_9CO)N(R_{10})$ (with $R_9$=$C_1$- to $C_6$-alkyl, $C_1$- to $C_4$-haloalkyl, optionally substituted phenyl or hydrogen and with $R_{10}$=hydrogen or $C_1$- to $C_4$-alkyl) and $R_{11}$ represents hydrogen, an alkali metal or a tri-$C_1$–$C_4$-alkylsilyl radical are reacted with a perhaloalkene of the formula (III)

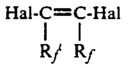

(III)

in which $R_f$ and $R_f'$ have the meaning indicated in formula (I) and

Hal represents fluorine, chlorine, bromine and/or iodine, in basic medium and in the presence of a solvent and if appropriate a derivatization and/or rederivatization are subsequently carried out, where the reaction of unsubstituted phenol and unsubstituted phenoxides (formula (II), $R_1''$ to $R_5''$=H, $R_1$=H or alkali metal) with octafluorocyclopentene (formula (III)), $R_f$ and $R_f'$ together =$(CF_2)_3$, Hal=F) is excluded.

Inasmuch as $R_1''$ to $R_5''$ in formula (II) have the same meaning as $R_1$ to $R_5$ in formula (I), $R_1''$ to $R_5''$ preferably represent that which is indicated as preferred in the corresponding disclosure for $R_1$ to $R_5$. $R_{11}$ preferably represents sodium or potassium.

In formula (III), Hal preferably represents fluorine, chlorine and/or bromine, in particular fluorine and/or chlorine. $R_f$ and $R_f'$ preferably denote that which is described as preferred in formula (I).

The basic medium required for the process according to the invention can be produced in different ways. In the use of compounds of the formula (II) with $R_{11}$=alkali metal (i.e. phenoxides which are basic), further measures for the production of a basic medium are not absolutely necessary. In the use of compounds of the formula (II) with $R_{11}$=hydrogen (i.e. phenols) or with $R_{11}$=tri-$C_1$-$C_4$-alkylsilyl, it is necessary to add basic substances. In general, bases are employed approximately in the stoichiometrically required amount, for example 1.7 to 2.3 moles of base per mole of the compound of the formula (III). If acidic hydrogen atoms are present in the compound of the formula (II) employed, at least the amount of base necessary for their neutralization is additionally expediently added, since otherwise undesired side reactions may result.

Possible bases are all types of inorganic and organic alkaline-reacting substances, for example oxides, hydroxides, carbonates and hydrogen carbonates of alkali metals and alkaline earth metals and amines, in particular tertiary amines. Alkali metal hydroxides, alkali metal carbonates, triethylamine and pyridine are preferred. Sodium hydroxide and triethylamine are particularly preferred.

If phenoxides are employed (formula (II), $R_{11}$=alkali metal), these can be obtained from the corresponding phenols in various ways. For example, the phenols can be reacted with alkali metals, alkali metal hydroxides, alkali metal hydrides or alkali metal alkoxides. Reactions with sodium, sodium hydroxide, sodium hydride, sodium methoxide or sodium ethoxide are preferred in this case.

Possible solvents are, for example, inert organic solvents, in special cases in combination with water. Suitable solvents are, for example, ethers, hydrocarbons, chlorinated hydrocarbons, nitriles, amides, sulphones and organic carbonates. Examples which may be mentioned are: methyl tert.-butyl ether, diethyl ether, tetrahydrofuran, dioxane, methylene chloride, trichloroethylene, chloroform, carbon tetrachloride, benzene, toluene, xylene, acetonitrile, dimethylformamide, tetramethylene sulphone, tetramethylurea, hexamethylphosphoramide and propylene carbonate. Preferred solvents are diethyl ether, methylene chloride, acetonitrile and dimethylformamide.

The process according to the invention can be carried out, for example, at temperatures in the range from −78 to +40° C. Preferably, the process is carried out at 0° to 25° C. If the process is carried out under elevated pressure, the reaction temperature can also be raised substantially above 40° C., for example up to 150° C.

The molar ratio of the compound of the formula (II) employed in each case to the compound of the formula (III) employed in each case may be, for example, 1.9:1 to 3:1. Preferably, stoichiometric amounts are employed, that is 2 moles of the compound of the formula (II) per mole of compound of the formula (III). The process according to the invention can also be carried out in such a way that in a first step only one Hal from the compound of the formula (III) is replaced by an aryloxy radical corresponding to the phenol or phenoxide of the formula (II) and in a second step the second Hal of the compound of the formula (III) is replaced by an identical or another aryloxy radical such as introduced in the first step. In the two-step process variant, a procedure can, for example, be used in which in the first step only a maximum of 1 mole of a compound of the formula (II) is employed per mole of a compound of the formula (III) and in the second step at least a further mole of the same or another compound of the formula (III) is employed. By addition of the necessary amount of base in two approximately equal portions, a 2-step procedure can be followed.

Not all fluorinated bisaryloxy-substituted alkenes of the formula (I) are directly accessible from a corresponding phenol or phenoxide of the formula (II) and a corresponding perhaloalkene of the formula (III). Compounds of the formula (I) which contain, for example, COOH, $NH_2$ having acidic H atoms, NCO, OH and/or $SO_3H$ groups must, under certain circumstances, according to the synthesis of the bisaryloxy-alkene structure be derivatized or rederivatized. Examples of this are the introduction of $SO_3H$ groups by reaction with sulphuric acid, the reduction of $NO_2$ to $NH_2$ groups, the ether cleavage of alkoxy to OH groups, the oxidation of $CH_3$ to COOH groups and the acidification of $SO_3Na$, COONa, $SO_3NR_3H$ or $COO(NR_3H)$ groups to form $SO_3H$ or COOH groups, the hydrolysis of carboxylic acid esters or nitriles to carboxylic acids, the phosgenation of $NH_2$ to NCO groups and the oxidation of S-alkyl to $SO_2Cl$ groups using elemental chlorine in water.

Compounds of the formula (I) which are in principle accessible by direct synthesis from a compound of the formula (II) and a compound of the formula (III) can also be obtained by derivatization or rederivatization. For example, 1,2-bis(4-carboxyphenoxy)-3,3,4,4,5,5-hexafluorocyclopent-1-ene can be prepared either by reacting methyl 4-hydroxybenzoate with 1,2-dichloro-3,3,4,4,5,5-hexafluorocyclopent-1-ene or octafluorocyclopentene and subsequently hydrolysing or by reacting Na 4-methylphenoxide with octafluorocyclopentene and subsequently oxidizing the methyl groups in the 1,2-bis(4-methylphenoxy)-3,3,4,4,5,5-hexafluorocyclopent-1ene obtained using potassium permanganate or chromium trioxide in $H_2SO_4$.

A preferred embodiment of the process according to the invention for the preparation of fluorinated bisaryloxysubstituted alkenes of the formula (I) is characterized in that a phenol or phenoxide of the formula (II) in which a radical from the group $R_1''$ to $R_5''$ does not denote hydrogen and has a $\sigma$ value of greater than 0.20 or in which a number of radicals from the group $R_1''$ to $R_5''$ do not denote hydrogen and at least half of these radicals have a $\sigma$ values of greater than 0.20 is reacted with a perhaloalkene of the formula (III) with the addition of 1.7 to 2.3 moles of a base per mol of the compound of the formula (III) and in the presence of an inert organic solvent and, if appropriate, a derivatization and/or rederivatization is subsequently carried out.

A further preferred embodiment of the process according to the invention for the preparation of fluorinated bisaryloxy-substituted alkenes of the formula (I) is characterized in that a phenoxide ($R_{11}$=an alkali metal) of the formula (II) in which a radical from the group $R_1''$ to $R_5''$ does not denote hydrogen and has a $\sigma$ value of less than 0.20 or in which a number of radicals from the group $R_1''$ to $R_5''$ do not denote hydrogen and at least half of these radicals have $\sigma$ values of less than 0.20 is reacted with a perhaloalkene of the formula (III) in the presence of a polar aprotic solvent and, if appropriate, a derivatization and/or rederivatization is subsequently carried out.

The $\sigma$ values of all types of substituents are illustrated and stated, for example, in J. March, Advanced Organic Chemistry, 2nd edition (1977), McGraw-Hill Kogakusha, pages 251 ff.

Possible aprotic solvents are, for example, acetonitrile, dimethylformamide, tetramethylene sulphone, hexamethylphosphoramide, tetramethylurea or propylene carbonate.

A further preferred embodiment of the process according to the invention for the preparation of fluorinated bisaryloxy-substituted alkenes of the formula (I) is characterized in that the phenol of the formula (II) is employed as a tri-$C_1$-$C_4$-alkylsilylether ($R_{11}$=for example, trimethylsilyl) which is cleaved in situ by bases, for example triethylamine. This process may then be advantageous if the free phenols of the formula (II) are unstable or relatively weakly reactive.

Finally, a particular embodiment of the process according to the invention for the preparation of bisaryloxy-substituted alkenes of the formula (I) is further also characterized in that any phenol ($R_{11}$=hydrogen) of the formula (II) and a perhaloalkene of the formula (III) are initially introduced together in an organic, water-immiscible solvent and 1.7 to 2.3 moles of alkali in the form of an aqueous solution and a phase-transfer catalyst are added to this.

Suitable phase-transfer catalysts are, for example, crown ethers such as 1,4,7,10,13,16-hexacyclooctadecane (18-crown-6), dicyclohexyl-18-crown-6, dibenzo-18-crown-6 and similar macrocyclic polyethers (see Pedersen, J.A.C.S. 89, 2495 and 7017 (1967)), and quarternary ammonium salts, for example the tetraalkylammonium chlorides, bromides, hydrogen sulphates and hydroxides which may contain identical or different alkyl groups having, for example, 1 to 16 C atoms and where an alkyl group can also be a benzyl group.

The present invention furthermore relates to the use of the new fluorinated bisaryloxy-substituted alkenes of the formula (I) as electrical insulating agents. The compounds of the formula (I) can be used, for example, as impregnating agents for condenser dielectrics, in particular for high tension condensers, and as a fluid for transformer cooling. In this connection, they are particularly suitable for reasons of their flame resistance (flash point above 250° C.) and thermal stability, their low viscosity, the simple accessibility in high purities, their absorption ability for hydrogen resulting from silent discharges in an electrical field, their inert behavior and their dielectric constants.

EXAMPLES

EXAMPLE 1

Preparation of 1,2-bis(4-bromophenoxy)-3,3,4,4,5,5-hexafluorocycloagent-1-ene 86.5 g of 4-bromophenol (0.5 mol) and 50.5 g of triethylamine were dissolved in 300 ml of methylene chloride at 5° C. 53 g of perfluorocyclopentene (0.25 mol) were added dropwise at 5° C. in the course of 25 minutes. The temperature was then allowed to climb at room temperature and the mixture was stirred at room temperature for 18 hours. For working up, the mixture was washed successively with 200 ml of water, 100 ml of 10% strength by weight sodium hydroxide solution, 100 ml of 5% strength by weight hydrochloric acid and again with 200 ml of water, and the organic phase was then dried and concentrated, and the residue was fractionally distilled. 68 g of product were obtained at a boiling point of 132° to 135° C. at 0.04 mbar (=52.5% of theory). Mass spectrometry gave a value for m/e of 516 for the molecular ion. The $^{19}F$ nuclear magnetic resonance spectrum showed characteristic bands at $\delta=-36.1$ ppm and at $\delta=-51.7$ ppm, measured against trifluoroacetic acid as external standard.

EXAMPLE 2

Preparation of 1,2-bis-(3,4-dimethylphenoxy)-3,3,4,4,5,5-hexafluorocyclopent-1-ene 48.8 g of 3,4-dimethylphenol (0.4 mol) were dissolved in 100 ml of methanol and converted into the corresponding sodium salt using 72 g of 30% strength by weight sodium methoxide solution. 66 g of this sodium salt were dissolved in 150 ml of dimethylformamide and 42.4 g of perfluorocyclopentene (=0.2 mol) were added at 3° to 10° C. in the course of 45 minutes. After warming to room temperature, the mixture was stirred at room temperature for 18.5 hours. For working up, the mixture was stirred into 300 ml of water, the organic phase was separated off, the aqueous phase was washed with 100 ml of methylene chloride, and the separated organic phase and the methylene chloride phase were combined and washed successively with 100 ml of water, 50 ml of 10% strength by weight sodium hydroxide solution and again with 100 ml of water. The crude product thus obtained was recrystallized from toluene. 42 g of product (=50.5% of theory) having a melting point of 65° to 67° C. were obtained Mass spectrometry gave a value for m/e of 416 for the molecular ion. The $^{19}F$ nuclear magnetic resonance spectrum showed characteristic bands at $\delta=-36.0$ ppm and at $\delta=-51.8$ ppm, measured against trifluoroacetic acid as external standard.

EXAMPLE 3

Preparation of 1,2-bis-[4-(1-methylethen-1-yl)-phenoxy]-3,3,4,4,5,5-hexafluorocyclopent-1-ene 41.4 g (0.2 mol) of 4-(1-methylethen-1-yl)-phenol trimethylsilylether and 20.2 g (0.2 mol) of triethylamine were initially introduced at 5° C. in 100 ml of methylene chloride. 21.2 g (0.1 mol) of perfluorocyclopentene were added dropwise at 5° C. in the course of 15 minutes and the temperature was then allowed to climb to room temperature. The mixture was then stirred for 17 hours at reflux at reflux (40° C.). For working up, the reaction mixture was washed successively with 100 ml of water, 50 ml of 5% strength by weight hydrochloric acid and again with 100 ml of water. The methylene chloride phase was dried over sodium sulphate and filtered, and the solvent was stripped off. The highly viscous crude product (41 g) was distilled in an oil pump vacuum. 35 g (=79.5% of theory) of a highly viscous oil having a boiling point of 130° to 145° C. at 0.05 mbar were obtained. The $^{19}F$ nuclear magnetic resonance spectrum showed characteristic bands at $\delta=-36.4$ ppm and $\delta=-52.0$ ppm, measured against trifluoroacetic acid as external standard.

EXAMPLE 4

Preparation of 1,2-bis-[4-(thiomethyl)phenoxy]-3,3,4,4,5,5-hexafluorocyclopent-1-ene 70 g of 4-thiomethylphenol (0.5 mol) were dissolved in 100 ml of methanol with warming and 90 of a 30% strength by weight sodium methoxide solution were added. The mixture was evaporated to dryness on a rotary evaporator, 87 g of sodium 4-thiomethylphenoxide remaining. This was dissolved in 150 ml of dimethylformamide, 53 g of perfluorocyclopentene (=0.25 mol) were added at 5° C. in the course of 45 minutes, then the mixture was warmed to room temperature and stirred at room temperature for 20 hours. The mixture was then poured into 300 ml of water, the aqueous mixture was filtered, the filtrate was extracted using 100 ml of methylene chloride, the methylene chloride phase was separated off, dried and concentrated, and the residue was fractionally distilled. 66 g of product were obtained at a boiling point of 110° to 120° C. at 0.04 mbar (=58.4% of theory). The $^{19}F$ NMR spectrum showed characteristic bands at $\delta=-38.8$ ppm and at $\delta=-51.5$ ppm, measured against trifluoroacetic acid as external standard. Mass spectrometry gave a value for m/e=452 for the molecular ion.

EXAMPLE 5

Preparation of 1,2-bis(4-formylphenoxy)-3,3,4,4,5,5-hexafluorocyclopent-1-ene 122 g of p-hydroxybenzaldehyde (1 mol) and 101 g of triethylamine were initially introduced at 5° C. in 400 ml of methylene chloride and 106 g of perfluorocyclopentene (0.5 mol) were added dropwise thereto in the course of 30 minutes. The mixture was then warmed to room temperature and stirred at room temperature for 20.5 hours. For working up, the mixture was added to 200 ml of water, and the organic phase was separated off and washed successively with 100 ml of 5% strength by weight hydrochloric acid and 200 ml of water, dried and evaporated to dryness on a rotary evaporator. The residue was recrystallized from 150 ml of toluene. 147 g of product having a melting point of 98° to 102° C. were thus obtained (=70.7% of theory). The mass spectrum gave a value for m/e=416 for the molecular ion, and the $^{19}F$ NMR spectrum gave characteristic bands at $\delta=-36.3$ ppm and at $\delta=-51.7$ ppm, measured against trifluoroacetic acid as external standard.

EXAMPLE 6

Preparation of 2,3-bis-(4-nitrophenoxy)-1,1,1,4,4,4-hexafluorobut-2-ene (cis/trans mixture)

0.1 mol of a mixture of hexafluorodibromobut-2-ene and hexafluorobromochlorobut-2-ene were added dropwise at 90° C. to 53.2 g (0.33 mol) of sodium p-nitrophenoxide, dissolved in 300 ml of dimethylformamide, and the mixture was subsequently stirred at this temperature for 16 hours. The reaction mixture was washed with 500 ml of 5% strength by weight sodium hydroxide solution and extracted with 1.5 l of ethyl acetate. After distilling off the ethyl acetate, 41.5 g of product (=95% of theory) were obtained. The mass spectrum gave a value for m/e of 438 for the molecular ion.

EXAMPLE 7

Preparation of 2,3-bis-(4-aminophenoxy)-1,1,1,4,4,4-hexafluorobut-2-ene (cis/trans mixture)

41.0 g (0.094 mol) of the compound obtained according to Example 6 were hydrogenated in 100 ml of methanol at 30 to 40 bar and 40° C. in the presence of 3 g of catalyst (5% by weight Pd on carbon). After filtering off the solid constituents, the solvent was distilled off and the residue was recrystallized from toluene. 23 g of product (=65% of theory) having a melting point of 191° to 195° C. were obtained. The $^{19}F$ nuclear magnetic resonance spectrum showed a characteristic band at $\delta=-14.2$ ppm, measured against trifluoroacetic acid as external standard.

EXAMPLE 8

Preparation of 1,2-bis-(4-nonylphenoxy)-3,3,4,4,5,5-hexafluorocyclopent-1-ene 121 g of sodium 4-nonylphenoxide (0.5 mol) were suspended in 250 ml of dimethylformamide and 53 g (0.25 mol) of perfluorocyclopentene were slowly added to this with stirring at 5° to 10° C. (addition time: 60 minutes). The mixture was then brought to room temperature and subsequently stirred for 8 hours. For working up, the reaction mixture was stirred into 400 ml of water, and the organic phase precipitated was separated off and taken up in 200 ml of methylene chloride. The methylene chloride solution was successively washed with 100 ml of 5% strength by weight sodium hydroxide solution and 200 ml of water and then dried over sodium sulphate, and the methylene chloride was stripped off on a rotary evaporator. The residue remaining was freed from lowboiling components at 0.05 mbar and 100° C. 62.5 g of product (=41% of theory) were obtained as a whitish cloudy highly viscous oil. The $^{19}F$ NMR spectrum showed characteristic bands at $\delta=-36.3$ ppm and at $\delta=-51.8$ ppm, measured against trifluoroacetic acid as external standard.

EXAMPLE 9

Preparation of 1,2-bis-(4-nitrophenoxy)-3,3,4,4-tetrafluorocyclobut-1-ene 81 g (0.5 mol) of hexafluorocyclobutene were introduced at 0° to 5° C. in the course of 30 minutes into 139 g (1mol) of 4-nitrophenol and 101 g (1 mol) of triethylamine, dissolved in 500 ml of methylene chloride. After 2 hours, the mixture was warmed to room temperature and subsequently stirred for a further 2 hours. For working up, the reaction mixture was washed successively twice with 200 ml each of water, once with 100 ml of 5% strength by weight hydrochloric acid and again with 200 ml of water and then dried over sodium sulphate, and the methylene chloride was removed on a rotary evaporator and a white crystalline solid was thus obtained. After recrystallizing from petroleum ether, the product was obtained in a yield of 75% of theory with a melting point of 112° to 115° C. The mass spectrum gave a value for m/e of 400 for the molecular ion and the $^{19}F$ NMR spectrum showed a band at $\delta=-35.5$ ppm, measured against trifluoroacetic acid as external standard.

EXAMPLE 10

Preparation of 1,2-bis-(4-chlorophenoxy)-3,3,4,4,5,5-hexafluorocyclopent-1-ene 106 g (0.5 mol) of perfluorocyclopentene were added dropwise at 0° to 5° C. to 128.5 g of 4-chlorophenol (1 mol) and 101 g of triethylamine (1 mol) in 300 ml of methylene chloride in the course of 60 minutes. The mixture was then slowly brought to room temperature and then stirred at 40° C. for 16 hours. For working up, the reaction mixture was washed twice with 200 ml each of water, then once with 100 ml of 5% strength hydrochloric acid and again with 200 ml of water and then dried over sodium sulphate, methylene chloride was stripped off on a rotary evaporator and the oil remaining was fractionally distilled in vacuo. 144 g of product (=66% of theory) were obtained with a boiling point of 113° to 115° C. at 0.03 mbar. The melting point of the product was 36° to 37° C. The mass spectrum gave a value for m/e of 428 ($^{35}Cl$), for the molecular ion. The $^{19}F$ NMR spectrum showed bands at $\delta=-36.1$ ppm and at $\delta=-51.7$ ppm, measured against trifluoroacetic acid as external standard.

The determination of the dielectric constant at 100 kHz, 1 V measuring voltage on a paste electrode at 40° C. gave a value of 4.06.

EXAMPLE 11

Preparation of 2,3-bis-[2,5-di(trifluoromethyl)-phenoxy]-1,1,1,4,4,4-hexafluorobut-2-ene (cis/trans mixture)

28 g (0.1 mol) of hexafluorobromochlorobut-2-ene were added dropwise at 80° C. to 46 g (0.2 mol) of sodium 2,5-di(trifluoromethyl)-phenoxide, dissolved in 150 ml of dimethylformamide and the mixture was subsequently stirred at this temperature for 4 hours. The reaction mixture was washed with 300 ml of 5% strength by weight sodium hydroxide solution and extracted using 1.5 l of ethyl acetate. After distilling off the ethyl acetate, 54.5 g of product (=88% of theory) were obtained. The product was purified by distillation; the boiling point was 63° to 69° C. at 0.1 mbar. The $^{19}F$ nuclear magnetic resonance spectrum showed characteristic bands at $\delta=+15.4$ ppm and at $+15.0$ ppm for the $CF_3$ groups, measured against trifluoroacetic acid as external standard. In the $^1-H$ nuclear magnetic resonance spectrum, the proton resonances of the aromatic were at $\delta=7.5$ ppm and at $\delta=7.75$ ppm, measured against tetramethylsilane as internal standard.

EXAMPLE 12

Preparation of 2,3-bis[4-(methyloxycarbonyl)-phenoxy]-1,1,1,4,4,4-hexafluorobut-2-ene (cis/trans mixture)

28 g (0.1 mol) of hexafluorobromochlorobut-2-ene were added dropwise at 80° C. to 30.4 g (0..2 mol) of sodium 4-(methyloxycarbonyl)-phenoxide, dissolved in 150 ml of dimethylformamide and the mixture was subsequently stirred at this temperature for 4 hours. The reaction mixture was washed with 300 ml of 5% strength by weight sodium hydroxide solution and extracted using 1.5 l of ethyl acetate, the ethyl acetate was distilled off and 44 g of product (=95% of theory) having a melting point of 123° C. were then obtained. The mass spectrum gave a value for m/e of 464 for the molecular ion.

EXAMPLE 13

Preparation of 1,2-bis-(4-fluorophenoxy)-3,3,4,4,5,5-hexafluorocyclopent-1-ene 112 g of 4-fluorophenol (1 mol) of 101 g of triethylamine were dissolved in 350 ml of methylene chloride at +50° C. 106 g of perfluorocyclopentene (0.5 mol) were added dropwise in the course of 45 minutes at 5° C.. The temperature was then allowed to climb to room temperature and the mixture was stirred at room temperature for 18 hours. For working up, the mixture was washed successively with 200 ml of water, 100 ml of 5% strength buy weight hydrochloric acid and again with 200 ml of water, then the organic phase was dried, concentrated and fractionally distilled. 125 g of product were obtained at a boiling point of 98° to 108° C. at 0.04 mbar (=63% of theory), which solidified in the receiver to give a solid having a melting point of 79° to 83° C. The mass spectrum gave a value for m/e of 396 for the molecular ion.

EXAMPLE 14

Preparation of 1,2-bis-(2,4-dichlorophenoxy)-3,3,4,4,5,5-hexafluorocyclopent-1-ene 212 g (1 mol) of perfluorocyclopentene were added dropwise at 0° to 5° C. to 326 g of 2,4-dichlorophenol (2 mol) and 202 g of triethylamine (2 mol) in 500 ml of methylene chloride in the course of 90 minutes. The mixture was then slowly brought to room temperature and then subsequently stirred at 40° C. for 16 hours. For working up, the reaction mixture was washed twice with 200 ml each of water, then with 200 ml of 5% strength by weight hydrochloric acid and again with 200 ml of water, and then dried over sodium sulphate, methylene chloride was stripped off on a rotary evaporator and the oil remaining was fractionally distilled in vacuo. 424 g of product having a boiling point of 136° to 138° at 0.03 mbar (=85% of theory) were obtained. The mass spectrum gave a value for m/e of 496 ($^{35}Cl$), for the molecular ion. The $^{19}F$ nuclear magnetic resonance spectrum showed characteristic bands at $\delta=-35.6$ ppm and at $\delta=-51.7$ ppm, measured against trifluoroacetic acid as external standard.

EXAMPLE 15

Preparation of 1,2-bis-(2,4,5-trichlorophenoxy)-3,3,4,4,5,5-hexafluorocyclopent-1-ene 424 g (2 mol) of perfluorocyclopentene were added dropwise at 0° to 5° C. to 790 g of 2,4,5-trichlorophenol (4 mol) and 404 g of triethylamine (4 mol) in 1800 ml of methylene chloride in the course of 120 minutes. The mixture was then slowly brought to room temperature and then subsequently stirred at 40° C. for 16 hours. For working up, the reaction mixture was washed twice with 500 ml each of water, then once with 500 ml of 5% strength by weight hydrochloric acid and again with 500 ml of water and then dried over sodium sulphate, methylene chloride was stripped off on a rotary evaporator and the oily residue remaining was recrystallized from a little methylene chloride. 845 g of product (=75% of theory) having a melting point of 65° to 68° C. were obtained. The mass spectrum gave a value for m/e of 564 ($^{35}Cl$) for the molecular ion. The $^{19}F$ nuclear magnetic resonance spectrum showed bands at $\delta=-35.5$ ppm and at $\delta=-51.5$ ppm, measured against trifluoroacetic acid as external standard.

EXAMPLE 16

Preparation of 1,2-bis-[4-(methyloxycarbonyl)phenoxy]-3,3,4,4,5,5-hexafluorocyclopent-1-ene 320 g of perfluorocyclopentene (1.51 mol) were added dropwise at 5° to 10° C. from a cooled dropping funnel with stirring in the course of 60 minutes to 455 g of methyl p-hydroxybenzoate (3 mol) and 303 g of triethylamine (3 mol) in 1000 ml of methylene chloride. After warming to room temperature, the reaction mixture was subsequently stirred at 40° C. for a further 16 hours, then washed twice with 300 ml each of water, once with 200 ml of 5% strength by weight hydrochloric acid and again with 300 ml of water. The mixture was then dried over sodium sulphate, the methylene chloride was stripped off on a rotary evaporator and 675 g of crude product (95% of theory) having a melting point of 67° to 74° C. were thus obtained. The crude product was recrystallized from 250 ml of toluene, resulting in a first crystal fraction of 360 g of product having a melting point of 88° to 92° C. and a second crystal fraction of 236.5 g having a melting point of 85° to 91° C. This corresponds to a total yield of recrystallized product of 83%. The mass spectrum for this product gave a value for m/e of 476 for the molecular ion.

EXAMPLE 17

Preparation of 1,2-bis-(4-methylphenoxy)-3,3,4,4,5,5-hexafluorocyclopent-1-ene 106 g of perfluorocyclopentene (0.5 mol) were slowly added dropwise in the course of 60 minutes to 150.5 g (1 mol) of sodium 4-methylphenoxide, dissolved in 300 ml of dimethylformamide. After the slightly exothermic reaction has subsided, the mixture was warmed to room temperature in the course of 2 hours and then subsequently stirred at room temperature for 4 hours. The reaction mixture was stirred into 500 ml of water, the organic phase was taken up using 250 ml of methylene chloride, and the methylene chloride solution was washed with 100 ml of 5% strength by weight sodium hydroxide solution and then with 200 ml of water, dried over sodium sulphate and concentrated on a rotary evaporator The oil remaining distilled. 130 g of product having a boiling point of 104° to 108° C. at 0.2 mbar and having a melting point of 46° to 48° C. were obtained (=67% of theory). The mass spectrum gave a value for m/e of 388 for the molecular ion. The $^{19}F$ NMR spectrum showed bands at $\delta=-35.9$ ppm and at $\delta=-51.8$ ppm, measured against trifluoroacetic acid as external standard.

EXAMPLE 18

Preparation of 1,2-bis-[2-(trifluoromethyl)-4-nitrophenoxy]-3,3,4,4,5,5-hexafluorocyclopent-1-ene 70 g (0.33 mol) of perfluorocyclopentene were added dropwise at 0° C. to 5° C. with stirring in the course of 30 minutes from a cooled dropping funnel to 138 g (0.66 mol) of 2-trifluoromethyl-4-nitrophenol and 66.7 g of triethylamine (0.66 mol) in 300 ml of methylene chloride. After 30 minutes, the mixture was slowly warmed to room temperature and subsequently stirred at room temperature for 3 hours. The reaction mixture was successively washed twice with 200 ml each of water, once with 100 ml of 5% strength hydrochloric acid and then again with 100 ml of water and dried over sodium sulphate. After stripping off the solvent, a whitish-brown crude product remained in an amount of 135 g (=70% of theory) having a melting point of 95° to 110° C. Recrystallization from petroleum ether gave back 85% of this product having a melting point of 118° to 120° C. The mass spectrum gave a value for m/e of 586 for the molecular ion. The $^{19}F$ NMR spectrum showed bands at $\delta=+16.1$ ppm ($CF_3$), $-35.2$ ppm, measured against trifluoroacetic acid as external standard.

EXAMPLE 19

Preparation of 1,2-bis-[2-(trifluoromethyl)-4-aminophenoxy]-3,3,4,4,5,5-hexafluorocyclopent-1-ene 393 g (0.5 mol) of a product prepared according to Example 18 were hydrogenated in 800 ml of dioxane at 35° to 40° C. and 30 to 40 bar of hydrogen in a 1.7 l stainless steel autoclave for 6 hours in the presence of 20 g of Raney nickel. The hydrogenation mixture was then filtered, the dioxane was removed from the filtrate in vacuo and 260 g of crude product (=98.8% of theory) having a melting point of 88° to 93° C. were thus obtained. 100 g of this product were recrystallized from 200 ml of petroleum ether. The recovery was 85%, and the melting point was then 102° to 104° C. The mass spectrum of the purified product gave a value for m/e of 526 for the molecular ion.

EXAMPLE 20

Preparation of 1,2-bis-(4-carboxylphenoxy)-3,3,4,4,5,5-hexafluorocyclopent-1-ene 135 g (0.28 mol) of the product from Example 11 were dissolved in a mixture of 450 ml of dioxane and 100 ml of water and stirred at 80° to 90° C. for 30 minutes after the addition of 25 g of powdered sodium hydroxide (0.625 mol). The mixture was then cooled to room temperature and 50 ml of concentrated hydrochloric acid were slowly added. The precipitated product was filtered off with suction, washed with slightly acidified water and dried for 2 hours at 110° C. The crude yield was 118 g (=94% of theory) and the product had a melting point of 243° to 246° C. After recrystallizing from a mixture comprising approximately equal parts by volume of ethanol and water, the yield of product was 102 g (=80% of theory) and the melting point 246° to 248° C. The mass spectrum of the purified product gave a value of m/e of 448 for the molecular ion. The $^{19}F$ NMR spectrum showed bands at $\delta=-34.9$ ppm and $-50.7$ ppm, measured against trifluoroacetic acid as external standard.

EXAMPLE 21

Preparation of 1,2-bis-(4-nitrophenoxy)-3,3,4,4,5,5-hexafluorocyclopent-1-ene (a) 278 g (2 mol) of 4-nitrophenol and 202 jg of triethylamine (2 mol) in 800 ml of methylene chloride were initially introduced at 5° to 10° C. into a 2 l three-packed flask. 212 g of perfluorocyclopentene (1 mol) were added dropwise to this from a cooled dropping funnel with stirring in the course of 60 minutes. After about 70% of the addition, a precipitate began to deposit which dissolved again after warming to 25° C. The mixture was subsequently stirred at room temperature for 4 hours, then the methylene chloride solution was washed successively twice with 300 ml each of water, once with 200 ml of 5% strength hydrochloric acid and again with 300 ml of water and dried over sodium sulphate, and the methylene chloride was stripped off to dryness on a rotary evaporator. 425 g of crude product (=94.4% of theory) having a melting point of 117° to 121° C. remained. After crystallization from methylene chloride, the melting point of the product was 124° to 127° C. The m ass spectrum gave a value for m/e of 450 for the molecular ion. The $^{19}F$ NMR spectrum showed bands at $\delta=-35.8$ ppm and $-51.4$ ppm, measured against trifluoroacetic acid as external standard.

(b) 24.5 g of 1,2-dichloro-3,3,4,4,5,5-hexafluorocyclopent-1-ene (0.1 mol) were initially introduced at 10° C. in 50 ml of dimethylformamide. After the addition of 27.8 g of 4-nitrophenol (0.2 mol) and 11.2 g (0.2 mol) of finely powdered KOH, the mixture was slowly warmed to 50° C. with stirring and held at this temperature for 20 hours. The reaction mixture was then poured into 500 ml of water, methylene chloride was added, and the organic phase was separated off and washed successively with 100 ml of water water, 100 ml of 10% strength by weight sodium hydroxide solution and again with 100 ml of water. After drying over sodium sulphate the mixture was concentrated to dryness on a rotary evaporator.

Crude yield: 26 g, which corresponds to 57.8% of theory.

After recrystallization from petroleum ether, 22 g or purified product having a melting point of 118° to 123° C. were obtained, the spectroscopic data (mass spectrum and $^{19}F$ NMR spectrum) of which were identical with those of the product from Example 15*a*).

EXAMPLE 22

Preparation of 1,2-bis-(4-aminophenoxy)-3,3,4,4,5,5-hexafluorocyclopent-1-ene 420 g of the purified product from Example 15 were hydrogenated in 1600 ml of dioxane at 35° to 40° C. and 30 to 40 bar of hydrogen in a 3 l stainless steel autoclave for 5 hours in the presence of 40 g of Raney nickel. The hydrogenation mixture was then filtered, the dioxane was removed from the filtrate in vacuo and 358 g of crude product (=91.8% of theory) having a melting point of 78° to 83° C. were thus obtained. 50 g of this product were crystallized from 200 ml of cyclohexane. The recovery was 75%, and the melting point was then 94° to 97° C. The mass spectrum of the purified product gave a value for m/e of 390 for the molecular ion. The $^{19}F$ NMR spectrum showed bands at $\delta=-35.5$ ppm and $-51.7$ ppm, measured against trifluoroacetic acid as external standard.

EXAMPLE 23

Preparation of 1,2-bis-(4-isocyanatophenoxy)-3,3,4,4,5,5-hexafluorocyclopent-1-ene 195 g (0.5 mol) of product prepared and purified according to Example 16 were dissolved in 100 ml of chlorobenzene, and added dropwise at 0° C. to a well-stirred solution of 220 g (2.22 mol) of phosgene in 1000 ml of chlorobenzene in the course of 75 minutes. After completion of the cold phosgenation, the mixture was heated to 70° C. in the course of 30 minutes and further phosgene was introduced. The temperature was then increased to 120° C. and the hot phosgenation was concluded after heating to reflux for 1 hour. From 50° C., a clear solution was present, from 80° to 90° C. vigorous evolution of hydrogen chloride gas set in. After completion of the phosgenation, excess phosgene was driven off by blowing out with nitrogen and the chlorobenzene was distilled off in a water jet vacuum. The yield of crude product was 212 g (=96% of theory). The melting point of the crude product was 66° to 71° C.; it had a content of active NCO of 87%.

The purification of the product by fractional distillation gave, with 75% recovery, a product having a boiling point of 153° to 154° C. at 0.01 mbar, a melting point of 77° to 79° C., a content of active NCO of 98.4% and a mass spectrum having a value for m/e of 442 for the molecular ion.

EXAMPLE 24

Preparation of 1,2-bis-[4-(trans-2-carboxyethyl)-ethenylphenoxy]-3,3,4,4,5,5-hexafluorocyclopent-1-ene 5.2 g (0.01 mol) of 1,2-bis-(4-bromophenoxy)-3,3,4,4,5,5-hexafluorocyclopent-1-ene (prepared according to Example 10, 2.5 g (0.025 mol) of ethyl acrylate, 2.05 jg of anhydrous sodium acetate, 22.5 mg of palladium(II) acetate and 122.5 mg of tri-o-tolyl-phosphine were added under nitrogen to 20 ml of dimethylformamide. After heating to reflux for 6 hours under a nitrogen atmosphere, the reaction mixture was filtered hot. The solvent was stripped off from the filtrate in vacuo and the residue was taken up in methylene chloride. After extracting the methylene chloride phase twice by shaking with water, it was dried over sodium sulphate. After stripping off the methylene chloride and recrystallizing the residue from n-hexane/ ethanol, 1.5 g of product, which corresponds to 27% of theory, having a melting point of 117to 119° C. were obtained.

The $^1$H NMR spectrum showed characteristic bands at 1.33 ppm, 4.25 ppm, 6.29 ppm, 7.65 ppm, 7.28 ppm and 7.53 ppm, measured against tetramethylsilane as internal standard.

EXAMPLE 25

Preparation of 1,2-bis-[4-(2-hydroxy-2-methylbutin-4-yl)phenoxy]-3,3,4,4,5,5-hexafluorocyclopent -1-ene 39 g (0.075 mol) of 1,2-bis-(4-bromophenoxy)-3,3,4,4,5,5-hexafluorocyclopent-1-ene (obtained according to Example 1), 32 g (0.38 mol) of 2-methyl-3-butin-2-ol, 211 mg of $PdCl_2(PPh_3)_2$, 230 mg of CuI and 630 mg of triphenylphosphine were added under nitrogen to 100 ml of triethylamine. After heating to reflux for 24 hours, the reaction mixture was filtered and the filtrate was concentrated in vacuo. Recrystallization of the residue resulting here from n-hexane/ethyl acetate gave 19.1 g of product, which corresponds to 48% of theory, having a melting point of 108° to 113° C. The $^1$H NMR spectrum showed characteristic bands at 1.59 ppm, 6.63 ppm and 7.2 ppm, measured against tetramethylsilane as internal standard.

EXAMPLE 26

Preparation of 1,2-bis-(4-ethinylphenoxy)-3,3,4,4,5,5-hexafluorocyclopent-1-ene 10.5 g (0.02 mol) of the product from Example 19 were heated together with 0.6 g of sodium hydroxide in 50 ml of toluene for 2 hours, a mixture of toluene and acetone distilling off. The remaining reaction mixture was then filtered and the filtrate was concentrated in vacuo. 8 g of product were obtained, the $^1$H NMR spectrum of which exhibited characteristic bands at 3.05 ppm, 6.63 ppm and 7.28 ppm. The yield was 98% of theory.

EXAMPLE 27

Preparation of 1,2-bis-(4-cyanophenoxy)-3,3,4,4,5,5-hexafluorocyclopent-1-ene 71.4 g (0.6 mol) of p-hydroxybenzonitrile and 60.6 g of triethylamine were initially introduced at 5° C. in 200 ml of methylene chloride. 63.6 g (0.3 mol) of perfluorocyclopentene were added dropwise in the course of 30 minutes and the mixture was then stirred at room temperature for 19.5 hours. The mixture was successively washed with 200 ml of water, 100 ml of 5% strength by weight hydrochloric acid and again with 100 ml of water, dried and concentrated to dryness. The crude yield of product was 118.5 g. Recrystallization from 100 ml of toluene yielded 107 g of purified product having a melting point of 118° to 121° C. Mass spectrometry gave a value for m/e of 410 for the molecular ion. The $^{19}$F nuclear magnetic resonance spectrum showed characteristic bands at $\delta=-35.9$ ppm and at $\delta=-51.7$ ppm, measured against trifluoroacetic acid as external standard.

EXAMPLE 28

Preparation of 1,2-bis-[4(acetamino)phenoxy]-3,3,4,4,5,5-hexafluorocyclopent-1-ene 106 g (0.5 mol) of perfluorocyclopentene were added dropwise at 5° C. in the course of 30 minutes to 151 g (1 mol) of p-acetaminophenol and 101 g of triethylamine in 300 ml of methylene chloride. The mixture was subsequently stirred at room temperature for 3 hours and then at 40° C. for a further 17 hours. The precipitated solid was then filtered from the reaction mixture, and the separated solid was washed successively with 250 ml of water, 250 ml of 5% strength by weight hydrochloric acid and again with 250 ml of water and dried at room temperature. The crude yield was 217 g of product, which corresponds to 91.6% of theory, and the product had a melting point of 198° to 225° C.

The crude product was digested for 3 hours in 300 ml of boiling methylene chloride, filtered off again and dried at 100° C. 193 g of purified product having a melting point of 230° to 234° C. were obtained. The purified product was investigated by mass spectroscopy, a value for m/e of 474 resulting for the molecular ion.

EXAMPLE 29

Preparation of 1,2-bis-[4-(carbonylbenzyl)-phenoxy]-3,3,4,4,5,5-hexafluorocyclopent-1-ene 21 g of 4-hydroxyphenyl benzyl ketone (0.1 mol) and 10.1 g of triethylamine were initially introduced at 5° C. in 50 ml of methylene chloride and 10.5 g (0.05 mol) of perfluorocyclopentene were added dropwise. The mixture was then warmed to room temperature and stirred at room temperature for 17 hours. For working up, the mixture was added to 50 ml of water, and the organic phase was separated off and washed successively with 50 ml of water, dried and evaporated to dryness on a rotary evaporator. The residue was recrystallized from 50 ml of toluene. 18 g of product (=60.4% of theory) having a melting point of 97° to 104° C. were thus obtained. The mass spectrum gave a value for m/e of 596 for the molecular ion. The $^{19}$F nuclear magnetic resonance spectrum showed bands at $\delta=-36.3$ ppm and at $\delta=-51.6$ ppm, measured against trifluoroacetic acid as external standard.

EXAMPLE 30

Preparation of 1,2-bis-[2,5-di(trifluoromethyl)phenoxy]-3,3,4,4,5,5-hexafluorocyclopent-1-ene 63.6 g (0.3 mol) of perfluorocyclopentene were added dropwise at 0° to 5° C. to 138 g of 2,5-di(trifluoromethyl)phenyl (0.6 mol) and 60.6 g of triethylamine in 300 ml of methylene chloride in the course of 30 min. The mixture was then slowly brought to room temperature and subsequently stirred at 40° C. for 16 hours. For working up, 400 ml of water were added to the reaction mixture, whereupon the product precipitated out and was filtered off with suction. After taking up in toluene, the solution was washed with water and dried over sodium sulphate. The toluene was then stripped off on a rotary evaporator and the residue remaining was fractionally distilled in vacuo. 132 g of product (=69.6% of theory) having a boiling point of 80° to 85° C. at 0.03 mbar were obtained. The melting point of the product was 76 to 79° C. The mass spectrum gave a value for m/e of 632 for the molecular ion. The $^{19}$F NMR spectrum showed bands at $\delta = -36.7$ ppm, at $\delta = -52.5$ ppm and at $\delta = +14.1$ ppm ($CF_3$), measured against trifluoroacetic acid as external standard.

The determination of the dielectric constant at 100 kHz, 1 V measuring voltage on a paste electrode at 80° C. gave a value of 2.20.

EXAMPLE 31

Preparation of 1,2-bis-(4-methoxyphenoxy)-3,3,4,4,5,5-hexafluorocyclopent-1ene 49.6 g of 4-hydroxyanisole (0.4 mol) were dissolved with warming in 50 ml of methanol and 72 g of a 30% strength by weight sodium methoxide solution were added. The mixture was evaporated to dryness on a rotary evaporator and the sodium salt obtained was dissolved in 150 ml of dimethylformamide. 42.4 g of perfluorocyclopentene (0.2 mol) were added dropwise at 5° C. in the course of 45 minutes, then the mixture was warmed to room temperature and subsequently stirred at 40° for 20 h ours. The mixture was then poured into 300 ml of water and the aqueous mixture was filtered. 40 g of a pulverulent filter cake which was partially insoluble in ethanol remained. The ethanolic solution was evaporated to dryness and 18 g of a partially crystalline oil were thus obtained. The aqueous filtrate was extracted using 100 l of methylene chloride, and the methylene chloride phase was separated off, dried over sodium sulphate and concentrated to dryness on a rotary evaporator. A further 11 g of an oil were obtained. Both product fractions were combined and fractionally distilled. 21 g of product were obtained at a boiling point of 135° to 145° C. at 0.03 mbar (=25% of theory). The $^{19}$F NMR spectrum showed characteristic bands at $\delta = -35.6$ ppm and at $\delta = -51.6$ ppm, measured against trifluoroacetic acid as external standard. Mass spectrometry gave a value for m/e of 420 for the molecular ion.

EXAMPLE 32

Preparation of 1,2-bis-(3-nitrophenoxy)-3,3,4,4,5,5-hexafluorocyclopent-1-ene 139 g (1 mol) of 3-nitrophenol and 101 g of triethylamine (1 mol) in 400 ml of methylene chloride were initially introduced at 5° to 10° C. into a 1 l three-necked flask. 106 g (0.5 mol) of perfluorocyclopentene were added dropwise to this from a cooled dropping funnel with stirring in the course of 60 minutes. The mixture was subsequently stirred at room temperature for 16 hours, then the methylene chloride solution was successively washed twice with 200 ml each of water, once with 100 ml of 5% strength hydrochloric acid and again with 200 ml of water and dried over sodium sulphate, and the methylene chloride was stripped off to dryness on a rotary evaporator. 208 g of crude product remained (=92.4% of theory) having a melting point of 73° to 77° C. After recrystallization from ligroin, 90% of the product was recovered, and the melting point was then 79° to 83° C. The $^{19}$F NMR spectrum showed characteristic bands at $\delta = -35.7$ ppm and at $\delta = -51.5$ ppm, measured against trifluoroacetic acid as external standard.

EXAMPLE 33

Preparation of 1,2-bis-(3-aminophenoxy)-3,3,4,4,5,5-hexafluorocyclopent-1-ene 325 g (0.5 mol) of a crude product obtained according to Example 32 were hydrogenated in 800 ml of dioxane at 35° to 40° C. and 30 to 40 bar of hydrogen in a 3 l stainless steel autoclave in the presence of 20 g Raney nickel. The hydrogenation mixture was then filtered, the dioxane was removed from the filtrate in vacuo and 185 g of crude product (=94.9% of theory) were thus obtained as highly viscous oil. 150 g of this product were precipitated from 300 ml of ethanol by addition of 100 ml of water. 135 g of a pale yellow oil were recovered, which corresponds to 90%. The mass spectrum of the precipitated product gave a value for m/e of 390 for the molecular ion.

EXAMPLE 34

Preparation of 1-(4-cyanophenoxy)-2-[4-(methyloxycarbonyl)phenoxy]-3,3,4,4,5,5-hexafluorocyclopent -1-ene 15.2 g (0.1 mol) of methyl 4-hydroxybenzoate and 10.1 g of triethylamine in 100 ml of methylene chloride were added dropwise at 5° C. to 21.2 g of perfluorocyclopentene in 15 min. After stirring at room temperature for 4 hours, a solution of 11.9 g (0.1 mol) of 4-hydroxybenzonitrile and 10.1 g of triethylamine in 100 ml of methylene chloride was added dropwise to the reaction mixture and it was stirred at 40° C. for a further 16 hours. The methylene chloride solution was then washed successively with 100 ml of water, 50 ml of 5% strength hydrochloric acid and again with 100 ml of water, dried over sodium sulphate and evaporated to dryness on a rotary evaporator. The crude yield was 40.6 g. The product was recrystallized from toluene and 39.0 g of crystalline material having a melting point of 96° to 98° C. was thus obtained, which corresponds to 88% of theory.

The mass spectrum showed a value for m/e of 443 for the molecular ion, and the $^{19}$F NMR spectrum showed characteristic bands at $\delta = -36.1$ ppm, $\delta = -36.6$ ppm and $\delta = -51.7$ ppm, measured against trifluoroacetic acid as external standard.

EXAMPLE 35

Preparation of 1-(4-bromophenoxy)-2-[4-(methyloxycarbonyl)phenoxy]-3,3,4,4,5,5-hexafluorocyclopent -1-ene 21.2 g (0.1 mol) of perfluorocyclopentene were added dropwise to 17.3 g (0.1 mol) of 4-bromophenol and 10.1 g of triethylamine in 100 ml of methylene chloride in the course of 15 min. and the mixture was subsequently stirred at room temperature for 4 hours. A solution of 0.1 mol of methyl 4-hydroxybenzoate and 10.1 g of triethylamine in 100 ml of methylene chloride was then added dropwise to the reaction mixture and it was subsequently stirred at 40° C. for a further 16 hours. The methylene chloride solution was then washed with 100 ml of water, then 50 ml of 5% strength hydrochloric acid and again with 100 ml of water, dried over sodium sulphate and evaporated to dryness on a rotary evaporator. 48 g of an oil were obtained which was distilled in vacuo. In this way, 41 g of product having a boiling point of 128° to 140° C. at 0.02 mbar were obtained, which corresponds to 82.7% of theory.

The mass spectrum showed a value for m/e of 496 ($^{79}Br$) as molecular ion. In the $^{19}F$ NMR spectrum, characteristic bands occurred at $\delta=-34.4$ ppm, $\delta=-35.0$ ppm and $\delta=-50.6$ ppm, measured against trifluoroacetic acid as external standard.

EXAMPLE 36

Preparation of 1-(4-methylphenoxy)-2-(4-nitrophenoxy)-3,3,4,4,5,5-hexafluorocyclopent-1-ene 21.2 g (0.1 mol) of perfluorocyclopentene were added dropwise at 5° C. to 13 g (0.1 mol) of sodium 4-methylphenoxide in 50 ml of dimethylformamide in the course of 15 minutes. After stirring at room temperature for 8 hours, a solution of 13.9 (0.1 mol) of 4-nitrophenol and 10.1 g of triethylamine in 50 ml of dimethylformamide was added dropwise to the reaction mixture, which was stirred for a further 6 hours at 40° C. The reaction mixture was then stirred into 300 ml of water and the organic phase was separated off after addition of 100 ml of methylene chloride. The organic phase was then washed successively with 50 ml of water, 50 ml of 5% strength hydrochloric acid and again with 50 ml of water, dried over sodium sulphate and evaporated to dryness on a rotary evaporator. The crude yield of product was 34 g. It was recrystallized from petroleum ether and 20 g of crystalline material were thus obtained, which corresponds to 47.7% of theory. The crystalline material had a melting point of 72° to 76° C. and showed a value for m/e of 419 for the molecular ion in the mass spectrum.

EXAMPLE 37

Preparation of 1-(4-cyanophenoxy)-2-(4-cyclohexylphenoxy)-3,3,4,4,5,5-hexafluorocyclopent-1-ene 11.9 g (0.1 mol) of 4-hydroxybenzonitrile and 10.1 g of triethylamine in 50 ml of dimethylformamide were added dropwise at 5° C. in 15 minutes to 21.2 g of perfluorocyclopentene. After stirring at room temperature for 2 hours, 19.8 g (0.1 mol) of solid sodium 4-cyclohexylphenoxide were added to the reaction mixture which was stirred at 80° C. for a further 16 hours. The reaction mixture was then added to 100 ml of water, and the organic phase was taken up in 100 ml of methylene chloride, washed with 50 ml of 5% strength by weight hydrochloric acid, then with 50 ml of 10% strength by weight sodium hydroxide solution and then with 100 ml of water, dried over sodium sulphate and evaporated to dryness on a rotary evaporator. The crude yield was 36.0 g. The product was recrystallized from petroleum ether and 27 g of crystalline material having a melting point of 99° to 103° C. were thus obtained, which corresponds to 58% of theory. The mass spectrum showed a value for m/e of 467 for the molecular ion.

EXAMPLE 38

Preparation of [1,2-bis-(4-carboxylphenoxy)-3,3,4,4,5,5-hexafluorocyclopent-1-ene] disodium salt 190.4 g (0.4 mol) of the product from Example 11 were dissolved in a mixture of 500 ml of dioxane and 100 ml of water and the mixture was heated to reflux for 30 min. after addition of 3.2 g of powdered sodium hydroxide. The reaction mixture was then evaporated to dryness on a rotary evaporator. The yield of product was 195 g, corresponding to 99% of theory. The product had a melting point of about 280° C. A value for m/e of 492 for the molecular ion was found in the mass spectrum.

EXAMPLE 39

Preparation of 1,2-bis-[4-(pentyloxycarbonyl)-phenoxy]-3,3,4,4,5,5-hexafluorocyclopent-1-ene 21.2 g (0.1 mol) of perfluorocyclopentene were added dropwise at 0° to 5° C. in the course of 10 minutes to 41.6 g of pentyl p-hydroxybenzoate (0.2 mol) and 20.2 g of triethylamine (0.2 mol) in 200 ml of methylene chloride. After stirring at room temperature for 16 hours, the reaction mixture was washed successively with 100 ml of water, 100 ml of 5% strength by weight hydrochloric acid and again with 100 ml of water and then dried, the methylene chloride was then stripped off on a rotary evaporator and the remaining oil was distilled in vacuo. 30 g of product having a boiling point of 146° to 160° C. at 0.02 mbar were obtained, which corresponds to 51% of theory. The mass spectrum gave a value for m/e of 588 for the molecular ion. In the $^{19}F$ nuclear magnetic resonance spectrum bands occurred at $\delta=-36.0$ ppm and at $\delta=-51.5$ ppm, measured against trifluoroacetic acid as external standard.

EXAMPLE 40

Preparation of 1,2-bis-[4-(chlorocarbonyl)phenoxy]-3,3,4,4,5,5-hexafluorocyclopent-1-ene 112 g (0.25 mol) of the product from Example 14 were stirred at reflux for 16 hours with 150 g of thionyl chloride. Excess thionyl chloride was then distilled off at atmospheric pressure and then in a water jet vacuum. The residue was recrystallized from ligroin. 84 g of crystalline product were obtained, which corresponds to 69.3% of theory. The product had a melting point of 82° to 85° C. In the mass spectrum, a value for m/e of 484 ($^{35}Cl$) was determined for the molecular ion.

EXAMPLE 41

Preparation of 1,2-bis-(3,4-dicarboxylphenoxy)-3,3,4,4,5,5-hexafluorocyclopent-1-ene 36.4 g (0.2 mol) of 4-hydroxyphthalic acid were dissolved in 200 ml of dimethylformamide and 60.6 g (0.6 mol) of triethylamine were added at 5° C. 21.2 g (0.1 mol) of perfluorocyclopentene were added dropwise in the course of 15 minutes and the mixture was stirred at 50° C. for 18 hours. 20 ml of methylene chloride was then added, and the reaction mixture was washed with 200 ml of water, then with 200 ml of 10% strength by weight hydrochloric acid and then again with 200 ml of water and dried. After stripping off the solvent, 23 g of an oily solid remained which was recrystallized from hot water acidified with a little hydrochloric acid. 17 g of a white solid having a melting point of 110° to 115° C. were obtained, which corresponds to 31.7% of theory. A further 25 g of crude product could be obtained from the washing water after acidification and concentration. The recrystallized material showed bands at $\delta=-35.7$ ppm and $\delta=-51.4$ ppm in the $^{19}F$ nuclear magnetic resonance spectrum, measured against trifluoroacetic acid as external standard.

EXAMPLE 42

Preparation of 1,2-bis-(4-sulphophenoxy)-3,3,4,4,5,5-hexafluorocyclopent-1-ene 43.2 (0.3 mol) of 4-hydroxybenzenesulphonic acid (as a 65% strength aqueous solution) and 60.6 g (0.6 mol) of triethylamine were initially introduced at 5° C. in 200 ml of dimethylformamide. 31.8 g (0.15 mol) of perfluorocyclopentene were added dropwise in the course of 15 minutes and the mixture was subsequently stirred at 60° C. for 17 hours. 200 ml of methylene chloride were then added, and the reaction mixture was washed with 200 ml of water, then with 200 ml of 10% strength by weight hydrochloric acid and then again with 200 ml of water and dried. After stripping off the solvent on a rotary evaporator, 47.5 g of an oily crystalline residue remained, which was recrystallized from glacial acetic acid. 27.5 g of crystalline product having a melting point of 251° to 255° C. were obtained, which corresponds point of 251° to 255° C. were obtained, which corresponds to 35.3% of theory. A further 35 g of crude product were isolated from the washing water after acidification and concentration. The mass spectrum of the recrystallized material showed a value for m/e of 520 for the molecular ion.

EXAMPLE 43

Preparation of 1,2-bis-[(4-benzyloxy)phenoxy]-3,3,4,4,5,5,-hexafluorocyclopent-1-ene 200 g of hydroquinone monobenzylether (1 mol) were stirred for 30 minutes at 5° to 10° C. with 56.1 g of powdered potassium hydroxide in 500 ml of dimethylformamide. 106 g (0.5 mol) of perfluorocyclopentene was then added dropwise with stirring from a cooled dropping funnel int eh course of 60 min. The reaction mixture was slowly brought to room temperature and then stirred at 45° C. for a further 16 hours. The mixture was then stirred into 1000 ml of water, and the organic phase was separated off and taken up using toluene. The toluene was distilled off azeotropically to remove residual water. 232 g of a partly crystalline oil remained, which corresponds to 81.4% of theory. The mass spectrum showed a value of 572 for m/e for the molecular ion. In the $^{19}F$ NMR spectrum, characteristic bands occurred at $\delta=-35.9$ ppm and $\delta=-51.7$ ppm, measured against trifluoroacetic acid as external standard.

EXAMPLE 44

Preparation of 1,2-bis-(4-hydroxyphenoxy)-3,3,4,4,5,5-hexafluorocyclopent-1-ene (a) 143 g (0.25 mol) of the product from Example 31 were hydrogenolytically cleaved for 8 hours with 5 g of palladium on carbon catalyst (palladium content: 5% by weight) at a hydrogen pressure of 5 to 8 bar and a temperature of 30° to 40° C. in 300 ml of tetrahydrofuran. The reaction mixture was then filtered and the filtrate was evaporated to dryness on a rotary evaporator. 96 g of a partly crystalline product were obtained, which corresponds to 98% of theory. After decanting from ethanol/water (1:1), the product was recrystallized from toluene. 83 g of crystalline material having a melting point of 107° to 109° C. were obtained, which corresponds to 85% of theory. The mass spectrum showed a value for m/e of 392 for the molecular ion. In the $^{19}F$ nuclear magnetic resonance spectrum, characteristic bands occurred at $\delta=-36.4$ ppm and at $\delta=-51.8$ ppm, measured against trifluoroacetic acid as external standard.

(b) 100 g (1.0 mol) of hydroquinone were dissolved in 200 ml of methanol with heating and converted into the monosodium salt using 180 g of 30% strength by weight sodium methoxide solution. 132 g (1.0 mol) of the sodium salt were then added in portions at 5° C. to a mixture of 250 ml of dimethylformamide and 106 g (0.5 mol) of perfluorocyclopentene. After stirring at room temperature for 19 hours, the mixture was added to 500 ml of water, and the organic phase was separated off after addition of 1000 ml of methylene chloride and subsequently washed with 500 ml of water. After drying, the solvent was stripped off on a rotary evaporator. 177 g of a partly crystalline, oily material remained. For further purification, this was dissolved in 200 ml of ethanol and reprecipitated by addition of 100 ml of water. 143 g of a slightly oily product was obtained, which corresponds to 73% of theory. The spectroscopic data (mass spectrum and $^{19}F$ nuclear magnetic resonance spectrum) corresponded to the product from Example 44*a*).

EXAMPLE 45

Preparation of 1,2-bis-(4-[2(4-hydroxyphenyl)prop-2-yl]phenoxy)-3,3,4,4,5,5-hexafluorocyclopent -1-ene 45.6 of bisphenol A (0.2 mol) were dissolved in 100 ml of methanol with warming and 36 g of a 30% strength by weight sodium methoxide solution were added. The mixture was evaporated to dryness on a rotary evaporator, 61 g of monosodium bisphenol A remaining. This was dissolved in 100 ml of dimethylformamide, 21.2 g of perfluorocyclopentene (0.1 mol) were added at 5° C. in the course of 60 minutes, then the mixture was warmed to room temperature and stirred at room temperature for 18 hours. It was then warmed to 70° C. for 2 hours. The mixture was then stirred into 200 ml of water and the organic phase was separated off. The latter was taken up in methylene chloride, and the solution was washed with 100 ml of water, then with 50 ml of 5% strength by weight hydrochloric acid and then again with 100 ml of water and then dried. After stripping off the solvent on a rotary evaporator and drying in the vacuum of an oil pump at 100° C., 53 g of a glass-like, transparent residue remained, which corresponds to 90.7% of theory. The $^{19}F$ nuclear magnetic resonance spectrum showed characteristic bands at $\delta=-36.1$ ppm and at $\delta=-51.5$ ppm, measured against trifluoroacetic acid as external standard.

EXAMPLE 46

Preparation of 1,2-bis-(4-nitrophenoxy)-3,3,4,4,5,5,6,6,-octafluorocyclohex-1-ene 26.2 g (0.1 mol) of decafluorocyclohexene were introduced at 0° to 5° C. in the course of 15 minutes into 27.8 g (0.2 mol) of 4-nitrophenol and 20.2 g (0.2 mol) of triethylamine, dissolved in 200 ml of methylene chloride.

The mixture was warmed to room temperature and subsequently stirred for 16 hours. For working up, the reaction mixture was washed successively twice with 100 ml each of water once with 100 ml of 5% strength hydrochloric acid and again with 100 ml of water and dried over sodium sulphate, and the methylene chloride was stripped off to dryness on a rotary evaporator, 45 g of crude product (=90% of theory) having a melting point of 150°-165° C. remained. After crystallisation from methylenchloride, the melting point of the product was 158°-166° C.

The mass spectrum gave a value for m/e of 500 for the molecular ion. The $^{19}F$ NMR spectrum showed bands at $\delta=-37.1$ ppm and $-54.8$ ppm, measured against trifluoroacetic acid as external standard.

What is claimed is:

1. A fluorinated bis aryloxy-substituted alkene compound of the formula (I)

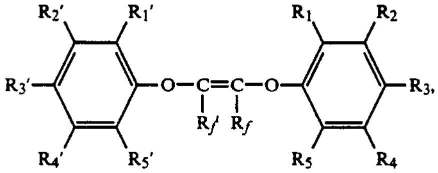

(I)

in which $R_1$ and $R_1'$ independently of one another represent a $C_1$- to $C_6$-perfluoroalkyl radical or $R_f$ and $R_f'$ together represent a $C_2$- to $C_4$-perfluoroalkylene radical and $R_1$ to $R_5$ and $R_1'$ to $R_5'$ independently of one another represent hydrogen, $C_1$- to $C_{12}$-alkyl, $C_2$- to $C_6$-alkenyl and/or $C_2$- to $C_6$-alkinyl, which are unsubstituted or substituted with OCN—, $R_6O$—, $H_2N$—, $R_6SO_3$— and/or $R_6OOC$— groups, with $R_6$=hydrogen or $C_1$- to $C_6$-alkyl or unsubstituted $C_5$- to $C_7$-cycloalkyl or $C_5$- to $C_7$-cycloalkyl substituted by $C_1$- to $C_6$-alkyl, $C_2$- to $C_6$-alkenyl, $C_1$- to $C_4$-haloalkyl, halogen, $NH_2$, COOH, OH, unsubstituted phenyl or phenyl substituted by one or more of $NO_2$, $NH_2$, NCO, COOH, CHO, OH, $SO_3H$, F, Cl or Br, and where the alkinyl groups may also contain trimethyl silyl substituents, $C_1$- to $C_4$-haloalkyl, $C_1$- to $C_4$-epoxyalkyl, $C_1$- to $C_4$-hydroxyalkyl, unsubstituted phenyl or phenyl substituted by one or more of $NO_2$, $NH_2$, NCO, COOH, CHO, OH, $SO_3H$, F, Cl or Br, $-OR_7$, with $R_7$=hydrogen, $C_1$- to $C_6$-alkyl, $C_1$- to $C_4$-hydroxyalkyl, $C_1$- to $C_4$-epoxyalkyl, $-(-CH_2-)_m-(-O-(-CH_2)_m-)_n-OH$ with m=1 to 4 and n=1 to 8, unsubstituted phenyl or phenyl substituted by one or more of $NO_2$, $NH_2$, NCO, COOH, CHO, OH, $SO_3H$, F, Cl or Br, or unsubstituted benzyl or benzyl substituted by one or more of $NO_2$, $NH_2$, NCO, COOH, CHO, OH, $SO_3H$, F, Cl or Br, CN, $SO_3X$, with X=hydrogen, sodium or potassium, S-$C_1$- to $C_6$-alkyl, $SO_2$—halogen, unsubstituted $C_5$- to $C_7$-cycloalkyl or $C_5$- to $C_7$-cycloalkyl substituted by $C_1$- to $C_6$-alkyl, $C_2$- to $C_4$alkenyl, $C_1$ to $C_4$-haloalkyl, halogen, $NH_2$, COOH, OH, unsubstituted phenyl or phenyl substituted by one or more of $NO_2NH_2$, NCO, COOH, CHO, OH, $SO_3H$, F, Cl or Br, carbonyl-$R_8$, with $R_8$=hydrogen, $C_1$- to $C_6$-alkyl, unsubstituted $C_5$- to $C_7$-cycloalkyl or $C_5$- to $C_7$-cycloalkyl substituted by $C_1$- to $C_6$-alkyl, $C_2$- to $C_6$-alkenyl, $C_1$- to $C_4$-haloalkyl, halogen, $NH_2$, COOH, OH, unsubstituted phenyl or phenyl substituted by one or more of $NO_2NH_2$, NCO, COOH, CHO, OH, $SO_3H$, F, Cl or Br, $C_1$- to $C_6$-alkoxy, $C_5$- to $C_7$-cycloalkoxy or OY with Y=hydrogen, sodium or potassium, or

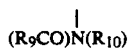

, with $R_9$=$C_1$- to $C_6$-alkyl to $C_4$-haloalkyl, unsubstituted phenyl or phenyl substituted by one or more of $NO_2$, $NH_2$, NCO, COOH, CHO, OH, $SO_3H$, F, Cl or Br or hydrogen and with $R_{10}$=hydrogen or $C_1$- to $C_4$-alkyl, where the compound is excluded in which $R_1$ to $R_5$ and $R_1'$ to $R_5'$ represent hydrogen and $R_f$ and $R_f'$ together represent $-(-CF_2-)_3-$.

2. A compounds according to claim 1, in which $R_f$ and $R_f'$ are identical and represent $CF_3$.

3. Compounds according to claim 1, in which $R_f$ and $R_f'$ together from a $-CF_2-CF_2-$ or a $-CF_2-CF_2-CF_2-$ group.

4. A compound according to claim 1, in which $R_1$ and $R_1'$ and independently thereof $R_5$ and $R_5'$ are identical and represent hydrogen, $C_1$- to $C_4$-alkyl, $C_1$- to $C_4$-haloalkyl, $NO_2$, NCO, fluorine or chlorine and in each case $R_2$ and $R_2'$ and independently thereof in each case $R_4$ and $R_4'$ are identical and represent hydrogen, $C_1$- to $C_4$-alkyl, COOH, fluorine, chlorine or $C_1$- to $C_4$-haloalkyl, and $R_3$ and $R_3'$ independently of one another represent hydrogen, $C_1$- to $C_{12}$-alkyl, $C_2$- to $C_6$-alkenyl and/or $C_2$- to $C_6$-alkinyl, which are unsubstituted or substituted by OCN—, $R_6O$—, $H_2N$—, $R_6SO_3$ and/or $R_6OOC$— groups, with $R_6$=hydrogen or $C_1$- to $C_6$-alkyl or unsubstituted $C_5$- to $C_7$-cycloalkyl or $C_5$- to $C_7$-cycloalkyl substituted by $C_1$- to $C_6$-alkyl, $C_2$- to $C_6$-alkenyl, $C_1$- to $C_4$-haloalkyl, halogen, $NH_2$, COOH, OH, unsubstituted phenyl or phenyl substituted by one or more of $NO_2NH_2$, NCO, COOH, CHO, OH, $SO_3H$, F, Cl or Br, and where alkinyl groups may also contain trimethyl silyl substituents, $C_1$- to $C_4$-haloalkyl, $C_1$- to $C_4$-epoxyalkyl, $C_1$- to $C_4$-hydroxyalkyl, unsubstituted phenyl or phenyl substituted by one or more of $NO_2$, $NH_2$, NCO, COOH, CHO, OH, $SO_3H$, F, Cl or Br, —$OR_7$, with $R_7$=hydrogen, $C_1$- to $C_6$-alkyl, $C_1$- to $C_4$-hydroxyalkyl, $C_1$- to $C_4$-epoxyalkyl, $-(-CH_2-)_m-(-O-(CH_2)_m-)_n-OH$ with m=1 to 4 and n=1 to 8, unsubstituted phenyl or phenyl substituted by one or more of $NO_2$, $NH_2$, NCO, COOH, CHO, OH, $SO_3H$, F, Cl or Br or unsubstituted benzyl or benzyl substituted by one or more of $NO_2NH_2$, NCO, COOH, CHO, OH, $SO_3H$, F, Cl or Br, CN, $SO_3X$, with X=hydrogen, sodium or potassium, S-$C_1$- to $C_6$-alkyl, $SO_2$-halogen, unsubstituted $C_5$- to $C_7$-cycloalkyl or $C_5$- to $C_7$-cycloalkyl substituted by $C_1$- to $C_6$-alkyl, $C_2$- to $C_6$-alkenyl, $C_1$- to $C_4$-haloalkyl, halogen, $NH_2$, COOH, OH, unsubstituted phenyl or phenyl substituted by one or more of $NO_2$, $NH_2$, NCO, COOH, CHO, OH, $SO_3H$, F, Cl or Br, carbonyl-$R_8$, with $R_8$=hydrogen, $C_1$- to $C_6$-alkyl, unsubstituted $C_5$- to $C_7$-cycloalkyl or $C_5$- to $C_7$-cycloalkyl substituted by $C_1$- to $C_6$-alkyl, $C_2$- to $C_6$-alkenyl, $C_1$- to $C_4$-haloalkyl, halogen, $NH_2$, COOH, OH, unsubstituted phenyl or phenyl substituted by one or more of $NO_2$, $NH_2$, NCO, COOH, CHO, OH, $SO_3H$, F, Cl or Br, $C_1$- to $C_6$-alkoxy, $C_5$- to $C_7$-cycloalkoxy or OY with Y =hydrogen, sodium or potassium or $$\overset{|}{(R_9CO)N(R_{10})}$$

, with $R_9$=$C_1$- to $C_6$-alkyl, $C_1$ to $C_4$-haloalkyl, unsubstituted phenyl or phenyl substituted by one or more of $NO_2$, $NH_2$, NCO, COOH, CHO, OH, $SO_3H$, F, Cl or Br or hydrogen and with $R_{10}$=hydrogen or $C_1$- to $C_4$-alkyl.

5. A compound according to claim 3, in which $R_f$ and $R_f'$ represent $CF_3$, $R_1$, $R_2$, $R_4$, $R_5$, $R_1$, $R_2$, $R_4'$ and $R_5'$ represent hydrogen and $R_3$ and $R_3'$ are identical and have a meaning indicated in claim 3 other than hydrogen.

6. Compounds according to claim 3, in which $R_f$ and $R_f'$ together denote a —$CF_2$—$CF_2$— or a —$CF_2$—$CF_2$—$CF_2$— group, $R_1$, $R_2$, $R_4$, $R_5$, $R_1'$, $R_2'$, $R_4'$ and $R_5'$ represent hydrogen and $R_3$ and $R_3'$ are identical and have a meaning indicated in claim 3 other than hydrogen.

* * * * *

UNITED STATES PATENT AND TRADEMARK OFFICE

CERTIFICATE OF CORRECTION

PATENT NO. : 4,990,633

DATED : February 5, 1991

INVENTOR(S) : Michael Negele, et al.

It is certified that error appears in the above-identified patent and that said Letters Patent is hereby corrected as shown below:

| | |
|---|---|
| Title Page, under "]75] Inventors:", line 2 | Delete "Beilefeldt" and substitute --Bielefeldt--. |

Signed and Sealed this

Fourteenth Day of September, 1993

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 4,990,633

DATED : February 5, 1991

INVENTOR(S) : Negele et al.

It is certified that error appears in the above-identified patent and that said Letters Patent is hereby corrected as shown below:

| | |
|---|---|
| Col. 10, lines 16-17 | Delete " hexafluorocycloagent " and substitute -- hexafluorocyclopent -- |
| Col. 10, line 17 | Begin new paragraph before " 86.5 g " |
| Col. 13, line 29 | Begin new paragraph before " 106 g " |
| Col. 15, line 25 | Delete " EXAM LE 1 " and substitute -- EXAMPLE 15 -- |
| Col. 16, line 60 | After " 35.2 ppm " insert -- and - 51.7 ppm -- |
| Col. 17, line 41 | Delete " 202 jg " and substitute -- 202 g -- |
| Col. 19, line 9 | Delete " 2.05 jg " and substitute -- 2.05 g -- |
| Col. 24, line 5 | Begin new paragraph before " 11.9 g " |
| Col. 27, line 67 | Delete " $R_1$ and $R_1'$ " and substitute -- $R_f$ and $R_f'$ -- |
| Col. 28, line 33 | Delete " $C_6$alkenyl " and substitute -- $C_6$-alkenyl -- |
| Col. 28, line 35 | Delete " $NO_2NH_2$ " and substitute -- $NO_2$, $NH_2$ -- |
| Col. 28, line 42 | Delete " $NO_2NH_2$, " and substitute -- $NO_2$, $NH_2$, -- |
| Col. 28, line 51 | After " $C_6$-alkyl " insert -- $C_1$ -- |
| Col. 28, claim 2 line 1 | Delete " compounds " and substitute -- compound -- |
| Col. 29, line 12 | Delete " $NO_2NH_2$, " and substitute -- $NO_2$, $NH_2$, -- |

UNITED STATES PATENT AND TRADEMARK OFFICE
CERTIFICATE OF CORRECTION

PATENT NO. : 4,990,633

DATED : February 5, 1991

INVENTOR(S) : Negele et al.

It is certified that error appears in the above-identified patent and that said Letters Patent is hereby corrected as shown below:

Col. 29, line 24 Delete " $NO_2NH_2$, " and substitute -- $NO_2$, $NH_2$, --

Col. 30, line 27 After " $R_4$, $R_5$, " delete " $R_1$, $R_2$ " and substitute -- $R_1$ , $R_2$ --

Signed and Sealed this

Twenty-sixth Day of October, 1993

Attest:

BRUCE LEHMAN

Attesting Officer

Commissioner of Patents and Trademarks